(12) United States Patent
Wookey et al.

(10) Patent No.: US 8,530,628 B2
(45) Date of Patent: Sep. 10, 2013

(54) DIAGNOSIS AND TREATMENT OF DISEASED AND DAMAGED TISSUE

(75) Inventors: Peter John Wookey, North Melbourne (AU); Anthony Zulli, Blackburn South (AU)

(73) Assignees: Welcome Receptor Antibodies Pty Ltd, North Melbourne (AU); Canterbury Medical Services Pty Ltd, Canterbury (AU)

( * ) Notice: Subject to any disclaimer, the term of this patent is extended or adjusted under 35 U.S.C. 154(b) by 396 days.

(21) Appl. No.: 12/680,520

(22) PCT Filed: Sep. 26, 2008

(86) PCT No.: PCT/AU2008/001435
§ 371 (c)(1),
(2), (4) Date: Oct. 22, 2010

(87) PCT Pub. No.: WO2009/039584
PCT Pub. Date: Apr. 2, 2009

(65) Prior Publication Data
US 2011/0059011 A1    Mar. 10, 2011

(30) Foreign Application Priority Data

Sep. 28, 2007 (AU) .............................. 2007905339
Oct. 9, 2007 (AU) .............................. 2007905527

(51) Int. Cl.
*C07K 16/00* (2006.01)
(52) U.S. Cl.
USPC ...................... 530/387.1; 530/388.1; 435/7.1
(58) Field of Classification Search
None
See application file for complete search history.

(56) References Cited

U.S. PATENT DOCUMENTS 5,869,045 A * 2/1999 Hellstrom et al. ......... 424/130.1

FOREIGN PATENT DOCUMENTS

WO    WO 2004/097422    11/2004

OTHER PUBLICATIONS

Rudikoff et al, Proc. Natl. Acad. Sci. USA, 79(6):1979-1983, Mar. 1982.*
Colman P. M. Research in Immunology, 145:33-36, 1994.*
Pascalis et al, Journal of Immunology, 2002, vol. 169, pp. 3076-3084.*
Casset et al, Biochemical and Biophysical Research Communications, 2003, vol. 307, pp. 198-205.*
Holm et al, Molecular Immunology, 2007, vol. 44, pp. 1075-1084.*
Paul, Fundamental Immunology, 3rd Edition, 1993, pp. 292-295, under the heading "Fv Structure and Diversity in Three Dimensions".*
Suzuki, et al., "Expression of calcitonin receptors on human myeloid leukemia cells", Journal of Biochemistry, 1995, vol. 118, No. 2 pp. 448-452.
Mould, et al., "Calcitonin receptor gene expression in K562 chronic myelogenous leukemic cells", Cancer Cell International, 2003, vol. 3 pp. 1-7.

* cited by examiner

*Primary Examiner* — Mark Halvorson
(74) *Attorney, Agent, or Firm* — Klauber & Jackson LLC

(57) ABSTRACT

The present invention relates to the diagnosis and treatment of leukemia and cardiovascular disease, as well as the detection of diseased and damaged tissue. More particularly, the present invention provides methods for targeting calcitonin receptor expressing cells for the diagnosis and treatment of leukemia or cardiovascular disease, and for stimulating wound healing. The invention also provides antibodies to calcitonin receptor expressing cells and methods of imaging or localizing cells expressing calcitonin receptor. Also provided is an enriched population of $CTR^+/CD34^+$ cells.

10 Claims, 7 Drawing Sheets

Figure 1:

K562 cells +/- 2mM Sod Butyrate (Mag X40)

- SB

+ SB

DIAGNOSIS AND TREATMENT OF DISEASED AND DAMAGED TISSUE

FIELD OF INVENTION

The present invention relates to methods of diagnosing, treating and/or preventing diseased or damaged tissue such as leukemia or cardiovascular disease, as well as methods of stimulating wound healing.

BACKGROUND OF THE INVENTION

Hematologic malignancies are cancers of the blood and bone marrow, including leukemia and lymphoma. Leukemia is a malignant neoplasm characterized by abnormal proliferation of leukocytes and is one of the four major types of cancer. Leukemia is diagnosed in about 29,000 adults and 2,000 children each year in the United States. Leukemias are classified according to the type of leukocyte most prominently involved. Acute leukemias are predominantly undifferentiated cell populations and chronic leukemias have more mature cell forms.

The acute leukemias are divided into lymphoblastic (ALL) and non-lymphoblastic (ANLL) types and may be further subdivided by morphologic and cytochemical appearance according to the French-American-British classification or according to their type and degree of differentiation. Specific B- and T-cell, as well as myeloid cell surface markers/antigens are used in the classification too. ALL is predominantly a childhood disease while acute myeloid leukemia (AML), is a more common acute leukemia among adults.

Chronic leukemias are divided into lymphocytic (CLL) and myeloid (CML) types. CLL is characterized by the increased number of mature lymphocytes in blood, bone marrow, and lymphoid organs. Most CLL patients have clonal expansion of lymphocytes with B cell characteristics. CLL is a disease of older persons. In CML, the granulocytic cells predominate at all stages of differentiation in blood and bone marrow, but may also affect liver, spleen, and other organs.

In patients with AML the immature myeloid, erythroid or megakaryotic cells severely outnumber erythrocytes (red blood cells) leading to fatigue and bleeding, and also to increased susceptibility to infection. In children as well as in adults AML has a poor prognosis despite the use of aggressive chemotherapeutic protocols. Overall survival rates are 40-60%. Autologous bone marrow transplant preceded by myeloablative chemotherapy does not change the survival but an allogeneic bone marrow transplant preceded by aggressive chemotherapy might increase the survival rates up to 70%. Unfortunately, the availability of a matched sibling donor is limited.

Among patients with leukemia there can be a highly variable clinical course as reflected by varying survival times and resistance to therapy. Reliable individual diagnostic and prognostic tools are limited at present. For example, there are several diagnostic or prognostic markers for AML, such as CD13, CD33, CD14, CD34, CD117 and CD7. However, the usefulness of these molecules as diagnostic and prognostic markers is limited because the association of these markers with AML has not been consistent (Mason et al., 2006). Accordingly, there remains a need for diagnostic and prognostic tools and for new treatments for leukemia.

The identification of cell types that play an integral role in pathological changes associated with diseased blood vessels such as intimal thickening, the formation of atherosclerotic plaque, in processes of plaque stabilization or rupture that results in obstructive thrombi, have been the subject of several investigations over the last two decades. However, in these pathogenic processes the characteristics of many of the molecular signals that drive migration and recruitment of cells into different vascular compartments are not clear.

A role for proliferation of precursor vascular smooth muscle cells in the genesis of atherosclerotic lesions has been reported (Ross and Glomset, 1973). The migration of blood-borne cells into the endothelium, neointima and media of atherosclerotic plaque has also been described in mouse models of vascular injury (Campbell et al, 2001). However, the mechanism for this is unclear.

Wound healing is the process through which the repair of damaged tissue(s) is accomplished. The wound healing process is comprised of three different stages, referred to as inflammation, granulation tissue formation, and matrix formation and remodelling. The healing process following trauma is an essential quality of and mechanism for life. Healing is associated with the migration into a lesion of blood-borne multi-potential precursor cells.

There is a need for new diagnostic tools and treatments for diseases in blood-borne precursor cells play a role. More particularly, there remains a need for diagnostic and prognostic tools and treatments for leukemia, and a need for further methods of diagnosing, treating and/or preventing diseased or damaged tissue such as cardiovascular disease, as well as methods of stimulating wound healing.

SUMMARY OF THE INVENTION

A new target on leukemia cells has now been identified and is useful in methods designed for the diagnosis or treatment of leukemia. This target is the calcitonin receptor (CTR).

Accordingly, the present invention provides a method for diagnosing or detecting leukemia in a subject, the method comprising determining the presence, timing and/or level of expression of calcitonin receptor in a sample obtained from the subject, wherein the presence, increased period and/or increased level of expression of calcitonin receptor is indicative of leukemia.

In one embodiment, diagnosing or detecting leukemia comprises contacting the sample with a compound that binds the calcitonin receptor.

The compound that binds the calcitonin receptor may be, for example, any polypeptide or molecule identified as having binding affinity to CTR. In one embodiment, the compound that binds CTR is an antibody.

The antibody may be a polyclonal or monoclonal antibody. Methods for raising such antibodies, for example in mice, rats, guinea pigs, rabbits, monkeys or humans, are known to those skilled in the art. In a preferred form of the invention, the antibody may be a monoclonal antibody. The antibody may be, for example, a chimeric antibody or a humanized antibody.

In one embodiment of the invention, the antibody binds an epitope of the calcitonin receptor comprising an amino acid sequence selected from SEQ ID NOs: 3, 5 and 7.

In a preferred embodiment, the antibody binds an epitope of the calcitonin receptor comprising an amino acid sequence selected from SEQ ID NOs: 5 and 7.

It will be understood that determining the presence, timing and/or level of expression of calcitonin receptor in a sample obtained from a subject may involve analysing nucleic acid, particularly mRNA, in a sample.

In one embodiment, determining the presence, timing and/or level of expression of calcitonin receptor in a sample obtained from the subject comprises contacting the sample with a nucleic acid probe that hybridises with a polynucleotide encoding the calcitonin receptor.

Preferably, the sample comprises bone marrow cells or blood. In a most preferred embodiment, the sample comprises bone marrow cells.

The present invention further provides a method for localizing leukemia cells in a subject, the method comprising administering to the subject a compound that binds calcitonin receptor, allowing the compound to bind to cells within the subject, and determining the location of the compound within the subject.

Preferably, the compound is detectably labelled.

The present invention further provides a method of treatment comprising:

(i) diagnosing or detecting leukemia according to a method of the invention; and (ii) administering or recommending a therapeutic for the treatment of leukemia.

The present invention further provides a method for monitoring the efficacy of treatment for leukemia in a subject, the method comprising treating the subject for leukemia and then detecting the presence, timing and/or level of expression of calcitonin receptor in a sample obtained from the subject, wherein an absence of, alteration in timing of and/or a reduction in the level of expression of calcitonin receptor after treatment when compared to before treatment is indicative of effective treatment.

The present invention further provides a method for treating or preventing leukemia in a subject, the method comprising administering to the subject an effective amount of a compound that binds calcitonin receptor to inhibit the growth of, or kill, leukemia cells in the subject.

In one embodiment, the compound is conjugated to a cytotoxic agent or biological response modifier. Preferably, the cytotoxic agent is a toxin, a chemotherapeutic agent, or a radioactive agent and the biological response modifier is a lymphokine, a cytokine, interferon, or growth factor.

In a preferred embodiment, the leukemia to be diagnosed, monitored or treated is non-chronic myelogenous leukemia (non-CML).

In another embodiment, the leukemia to be diagnosed, monitored or treated is acute myelogenous leukemia or acute lymphoblastic leukemia.

The present invention further provides a method for removing leukemia cells from a sample, the method comprising:

(i) exposing the sample to a compound that binds calcitonin receptor, and (ii) isolating a cellular fraction of the sample which does not bind the compound.

The present invention further provides a method for autologous hematopoietic cell transplantation in a subject, the method comprising:

(i) removing a hematopoietic precursor cell population from the subject, (ii) treating the cell population with a compound that binds calcitonin receptor, (iii) removing cells that bind the compound from the cell population, and (iv) transplanting the treated cell population from step (iii) into the subject.

In one embodiment, the compound binds an epitope of calcitonin receptor and the epitope comprises an amino acid sequence selected from SEQ ID NO: 3, SEQ ID NO: 5 (epitope 4) or SEQ ID NO: 7 (epitope 5).

Preferably the epitope comprises an amino acid sequence selected from SEQ ID NO:5 or SEQ ID NO: 7

In one embodiment, the compound is conjugated to a cytotoxic agent.

Preferably, the compound comprises an antibody or fragment thereof.

The present invention further provides use of a compound that binds calcitonin receptor for the manufacture of a medicament for the treatment or prophylaxis of leukemia.

The present invention further provides a method for identifying a candidate compound for the treatment of leukemia, the method comprising:

contacting a candidate compound with a calcitonin receptor or epitope thereof; and detecting binding of the candidate compound to the calcitonin receptor or epitope thereof.

The present inventor has identified epitopes on the extracellular domains of CTR that can be targeted by antibodies useful for identifying CTR on the surface of cells. In contrast, prior art anti-CTR antibodies have only been directed to epitopes in the cytoplasmic domain of CTR.

Accordingly, the present invention provides an antibody, or fragment thereof, which specifically binds calcitonin receptor, wherein the antibody or fragment thereof binds an epitope comprising SEQ ID NO:5 or SEQ ID NO:7. Preferably, the antibody or fragment thereof binds an epitope comprising SEQ ID NO:5.

In one embodiment, the antibody is a monoclonal antibody.

In another embodiment, the antibody is 1C11 or 9B4, or an antibody which comprises at least one complementarity determining region of 1C11 or 9B4.

In yet another embodiment, the antibody is detectably labelled.

The present invention further provides a stable antibody producing cell line which is capable of producing the antibody of the invention.

In one embodiment, the cell line is 1C11 as deposited with the European Collection of Cell Cultures (ECACC) under Deposit Reference 07081002, or 9B4 as deposited with the European Collection of Cell Cultures (ECACC) under Deposit Reference 07081001.

The present invention further provides an antibody that binds to calcitonin receptor, wherein the antibody competitively inhibits the binding of monoclonal antibody 1C11 to calcitonin receptor.

In another embodiment, the present invention provides an antibody that binds to calcitonin receptor, wherein the antibody competitively inhibits the binding of monoclonal antibody 9B4 to calcitonin receptor.

The comparative binding specificity of an antibody may be determined by, for example, antibody-antibody competition assays in the presence of calcitonin receptor or an epitope of calcitonin receptor.

The present invention further provides a method of localizing calcitonin receptor expressing cells in a sample obtained from a subject, the method comprising contacting the sample with the antibody or fragment thereof of the invention and detecting binding of the antibody to the calcitonin receptor.

In one embodiment, the sample comprises blood and/or bone marrow.

In a preferred embodiment, the sample is from a subject suspected of having leukemia.

The present invention further provides a method for localizing leukemia cells in a subject, the method comprising administering to the subject the antibody or fragment thereof of the invention, allowing the antibody or fragment thereof to bind to cells within the subject, and determining the location of the antibody or fragment thereof within the subject.

In yet another embodiment, the sample is obtained from a mammalian subject, for example a human subject.

The present invention further provides a method of isolating calcitonin receptor expressing cells from a sample, the method comprising:

contacting a sample comprising calcitonin receptor expressing cells with an antibody or fragment thereof of the invention under conditions sufficient for the antibody to bind to calcitonin receptor expressing cells.

Preferably, the cells also express CD34.

In one embodiment, the method further comprises isolating antibody-bound calcitonin receptor expressing cells from the sample.

The step of contacting the sample with the antibody or fragment thereof may be performed by any suitable technique known to those skilled in the art. For example, the sample and the antibody may be subject to gradient centrifugation. More particularly, peripheral blood mononuclear cells and/or bone marrow precursor cells may be partially purified, for example on a Ficoll-paque gradient using centrifugation.

The step of isolating antibody-bound $CTR^+$ cells from the sample may be performed by any suitable technique known to those skilled in the art. By way of example, $CTR^+$ cells may be isolated using a magnetic separation technique, such as the MAC system of magnetic capture (Miltenyi Biotec, Germany) of $CTR^+$ cells using antibodies that bind calcitonin receptor, or by flow cytometry such as fluorescence activated cell sorting (FACS).

The present inventors have identified a novel population of cells expressing both CTR and CD34.

Accordingly, the present invention further provides an enriched population of $CTR^+/CD34^+$ cells. Thus, in a further aspect the present invention provides an expanded cell population obtained by culturing the enriched population of $CTR^+/CD34^+$ cells.

Preferably, the cells are blast cells.

The present inventors have determined that cells expressing the calcitonin receptor (CTR) are also present in diseased and damaged tissues in addition to leukemia cells.

Accordingly, the present invention provides a method for detecting diseased or damaged tissue in a subject, the method comprising:

administering to the subject a compound that binds calcitonin receptor; and detecting the compound bound to the calcitonin receptor, wherein the presence of calcitonin receptor expressing cells in tissue is indicative of diseased or damaged tissue.

When the diseased or damaged tissue is vascular tissue, the calcitonin receptor expressing cells may be present in, for example, the endothelium, the neo-intima and/or the media of a blood vessel.

Preferably, the CTR+ cells are also CD34+.

Preferably, the compound is detectably labelled. However, in an embodiment the compound is not detectably labelled and the method further comprises administering a second compound that can be used to detect the binding of the anti-CTR compound to CTR. For example, the anti-CTR compound can be an antibody or CTR binding fragment thereof and the second compound is a detectably labelled secondary antibody which binds the anti-CTR antibody.

The present invention also provides a method for detecting diseased or damaged tissue in a subject, the method comprising determining the presence, timing and/or level of expression of calcitonin receptor in a sample obtained from the subject, wherein the presence, increased period and/or increased level of expression of calcitonin receptor is indicative of diseased or damaged tissue.

In one embodiment, the method comprises contacting the sample with a compound that binds the calcitonin receptor.

The compound that binds the calcitonin receptor may be, for example, any polypeptide or molecule identified as having binding affinity to CTR. In one embodiment, the compound that binds CTR is an antibody or CTR binding fragment thereof.

The antibody may be a polyclonal or monoclonal antibody. Methods for raising such antibodies, for example in mice, rats, guinea pigs, rabbits, monkeys or humans, are known to those skilled in the art. In a preferred form of the invention, the antibody may be a monoclonal antibody. The antibody may be, for example, a chimeric antibody or a humanized antibody.

In one embodiment of the invention, the antibody or CTR binding fragment thereof binds an epitope of the calcitonin receptor comprising, SEQ ID NO:3, SEQ ID NO:5 or SEQ ID NO:7.

In a preferred embodiment, the epitope of the calcitonin receptor comprises SEQ ID NO:5 or SEQ ID NO:7.

It will be understood that determining the presence, timing and/or level of expression of calcitonin receptor in a sample obtained from a subject may involve analysing nucleic acid, particularly mRNA, in a sample.

In one embodiment, determining the presence, timing and/or level of expression of calcitonin receptor in a sample obtained from the subject comprises contacting the sample with a nucleic acid probe that hybridises with a polynucleotide encoding the calcitonin receptor.

In an embodiment, the sample comprises blood, blood vessel and/or bone marrow. Preferably, the sample comprises blood vessel.

Preferably, the disease is cardiovascular disease.

Also provided is a method of treatment comprising:

detecting cardiovascular disease according to a method of invention; and administering or recommending a therapeutic treatment of cardiovascular disease.

In a further aspect, the present invention provides a method of treating and/or preventing cardiovascular disease in a subject, the method comprising administering to the subject a compound which modulates the activity, division of, or life span of calcitonin receptor expressing cells.

In an embodiment, the compound binds the calcitonin receptor.

In one embodiment, the method stabilizes atherosclerotic plaque, and hence reduces the risk of stroke.

The present inventors have shown that calcitonin receptor expressing cells migrate to sites of cardiovascular disease. Thus, these cells can be used to deliver agents to sites of such disease.

Accordingly, in a further aspect the present invention provides a method of treating and/or preventing cardiovascular disease in a subject, the method comprising administering to the subject a compound which binds calcitonin receptor expressing cells, wherein the compound comprises a cytotoxic agent or biological response modifier.

In another aspect, the present invention provides a method of treating and/or preventing cardiovascular disease in a subject, the method comprising administering to the subject genetically modified calcitonin receptor expressing cells, wherein the cells comprise at least one transgene encoding a cytotoxic agent or biological response modifier.

Examples of cytotoxic agents include, not are not limited to, toxins, chemotherapeutic agents, and radioactive agents.

Examples of biological response modifiers include, not are not limited to, lymphokines, cytokines, interferons and growth factors.

The present inventors identified CTR expressing cells in tubules of diseased media of blood vessels. This can be considered as a pre-condition or intermediate step in processes that lead to calcification of vessel walls. Accordingly, the present invention further provides a method of treating or preventing calcification of blood vessel in a subject, the method comprising administering to the subject a compound which modulates the activity, division of, or life span of calcitonin receptor expressing cells.

Also provided is the use of a compound which modulates the activity, division of, or life span of calcitonin receptor expressing cells for the manufacture of a medicament for the treatment and/or prevention of cardiovascular disease.

Preferably, the compound is an antibody or CTR binding fragment thereof. More preferably, the antibody is a monoclonal antibody.

In a further aspect, the present invention provides for the use of a compound which binds calcitonin receptor expressing cells for the manufacture of a medicament for the treatment and/or prevention of cardiovascular disease, wherein the compound comprises a cytotoxic agent or biological response modifier.

In another aspect, the present invention provides for the use of genetically modified calcitonin receptor expressing cells for the manufacture of a medicament for the treatment and/or prevention of cardiovascular disease, wherein the cells comprise at least one transgene encoding a cytotoxic agent or biological response modifier.

It has also been established that calcitonin receptor expressing cells are associated with wound healing.

Thus, in a further aspect the present invention provides a method of stimulating wound healing in a subject, the method comprising administering to the subject a compound which stimulates the activity and/or proliferation of calcitonin receptor expressing cells.

In another aspect, the present invention provides a method of stimulating wound healing in a subject, the method comprising administering to the subject a compound which binds calcitonin receptor expressing cells, wherein the compound comprises a biological response modifier.

In yet a further aspect, the present invention provides a method of stimulating wound healing in a subject, the method comprising administering to the subject calcitonin receptor expressing cells.

Preferably, the cells comprise at least one transgene encoding a biological response modifier.

Also provided is the use of a compound which stimulates the activity and/or proliferation of calcitonin receptor expressing cells for the manufacture of a medicament for stimulating wound healing in a subject.

In another aspect, the present invention provides for the use of a compound which binds calcitonin receptor expressing cells for the manufacture of a medicament for stimulating wound healing in a subject, wherein the compound comprises a biological response modifier.

In a further aspect, the present invention provides for the use of calcitonin receptor expressing cells for the manufacture of a medicament for stimulating wound healing in a subject.

In another aspect, the present invention provides a method for screening for a compound for the treatment and/or prevention of diseased or damaged tissue, the method comprising:
  contacting a candidate compound with a calcitonin receptor or fragment thereof; and
  detecting binding of the compound to the calcitonin receptor or fragment thereof.

In another aspect, the present invention provides a method for screening for a compound for the treatment and/or prevention of diseased or damaged tissue, the method comprising:
  contacting a candidate compound with a calcitonin receptor or fragment thereof; and
  determining whether the compound modulates the activity, division of, or life span of calcitonin receptor expressing cells.

Preferably, the disease is cardiovascular disease.

In a further aspect, the present invention provides a method for screening for a candidate compound for stimulating wound healing, the method comprising:
  contacting a candidate compound with a calcitonin receptor or fragment thereof; and
  detecting binding of the compound to the calcitonin receptor or fragment thereof.

In another aspect, the present invention provides a method for screening for a candidate compound for stimulating wound healing, the method comprising:
  contacting a candidate compound with a calcitonin receptor or fragment thereof; and
  determining whether the compound stimulates the activity or proliferation of calcitonin receptor expressing cells.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As will be apparent, preferred features and characteristics of one aspect of the invention are applicable to many other aspects of the invention.

The invention is hereinafter described by way of the following non-limiting Examples and with reference to the accompanying figures.

KEY TO THE SEQUENCE LISTING

SEQ ID NO: 1—nucleotide sequence of human CTR
SEQ ID NO: 2—amino acid sequence of human CTR
SEQ ID NO: 3—epitope 1 of human CTR
SEQ ID NO: 4—epitope 1 of rabbit CTR
SEQ ID NO: 5—epitope 4 of human CTR
SEQ ID NO: 6—epitope 4 of rabbit CTR
SEQ ID NO: 7—epitope 5 of human CTR
SEQ ID NO: 8—epitope 1 of rat CTR

BRIEF DESCRIPTION OF THE ACCOMPANYING DRAWINGS

FIG. 1. CTR expression in precursor cells of bone marrows of AML patients.

Figure 2:
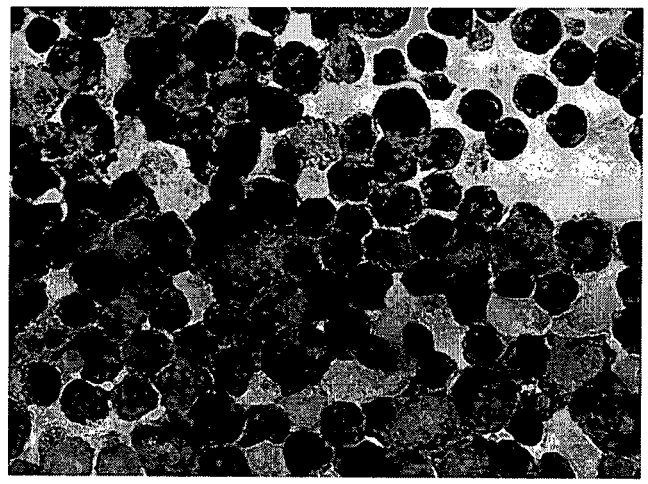
Figure 2:
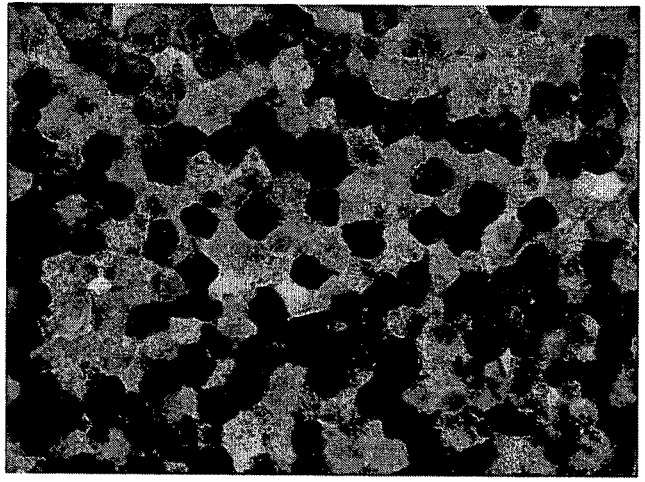

FIG. 2. CTR expression in myelogenous cell line K-562 stained with MAb 9B4.

Figure 3:
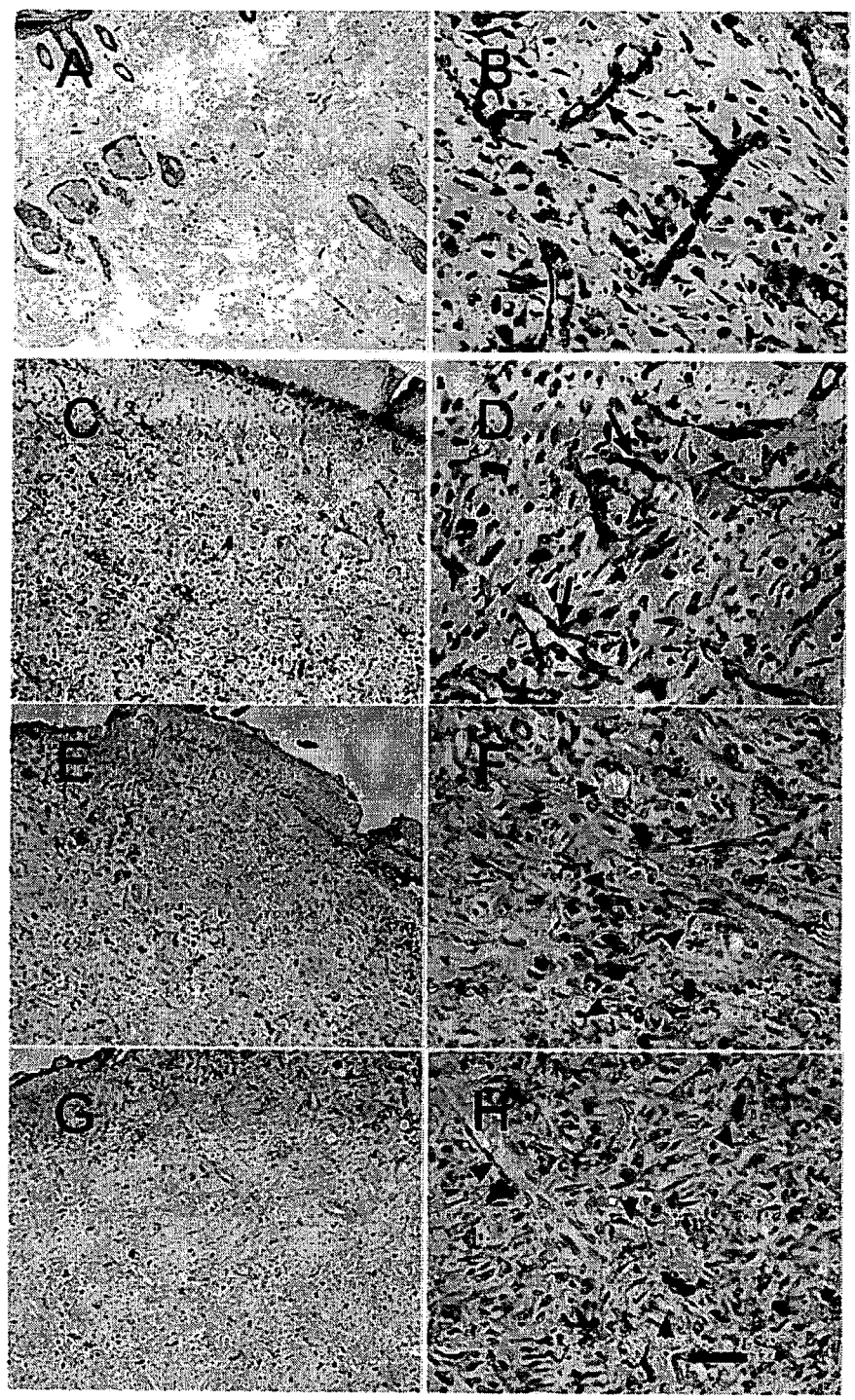

FIG. 3. The healing skin wounds of mice are represented in these images. Control tissue from a similar subcutaneous region of the back is shown in panel A. Shown in panels B (X40) and D (X40) are images from the same field as panel C (X10) seven days after healing had begun. Arrowed are examples of CTR-positive cells lining nascent blood vessels. Also apparent within this granulation tissue are CTR-positive cells that appear by shape as elongated myofibroblasts. By day 10 (panels E [X10] & F [X40]) the intensity of CTR expression had been reduced in the region of healing particularly in the endothelial cell population (arrowheads). Shown in panels G (X10) & H (X40) is the region of a wound twelve days after healing had commenced and there is evidence of a further decrease in the intensity of staining and/or the number of CTR-positive cells. Scale bar in A, C, E & G=190 μm and B, D, F & H=50 μm.

Figure 4:
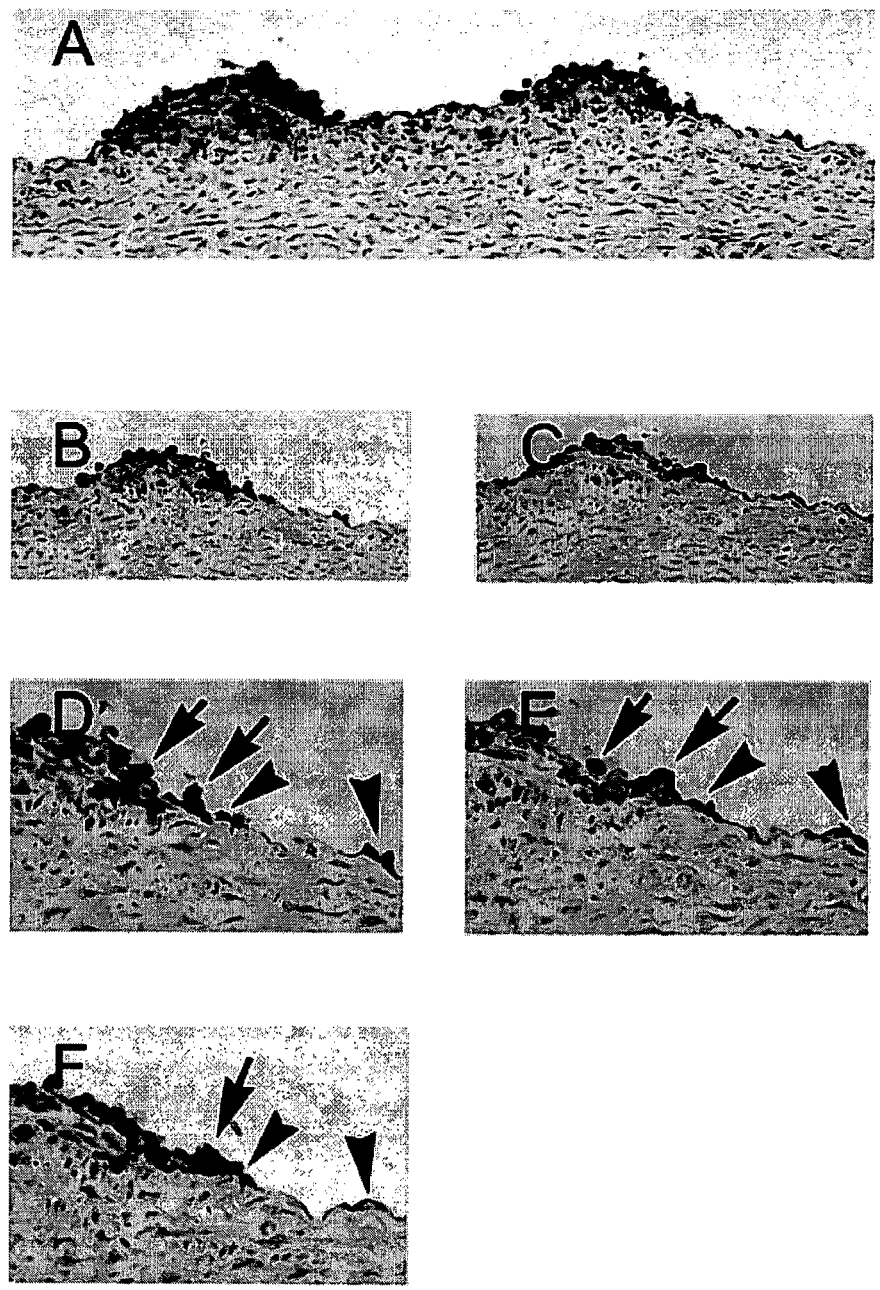

FIG. 4. The diseased abdominal arteries of rabbits fed a diet including 0.5% cholesterol for 4 weeks. Cells that stain CTR-positive are found concentrated around the endothelial layer of atherosclerotic plaques but are absent from the surrounding endothelium (panel A). Panels A (X40), B (X40) & D (X100) were stained using the antibody MAb 31-01 (MCA 2191, AbD Serotec) (diluted 1:500) which was raised against an intracellular epitope of CTR. The staining of a serial section [panels C (X40) & E (X100)] was developed using MAb 1C11 (1:250) which was directed against an extracellular epitope (epitope 4; SEQ ID NO: 5) of human CTR. In panel F (X100) the staining in an adjacent, but not serial section, was developed with a monoclonal anti-CD34 antibody (dilution 1:400). The arrows in panels D, E & F indicate identical foam cells that are CTR-positive. Arrowheads indicate putative endothelial cells that are CTR-positive in the region of the plaque.

Figure 5:
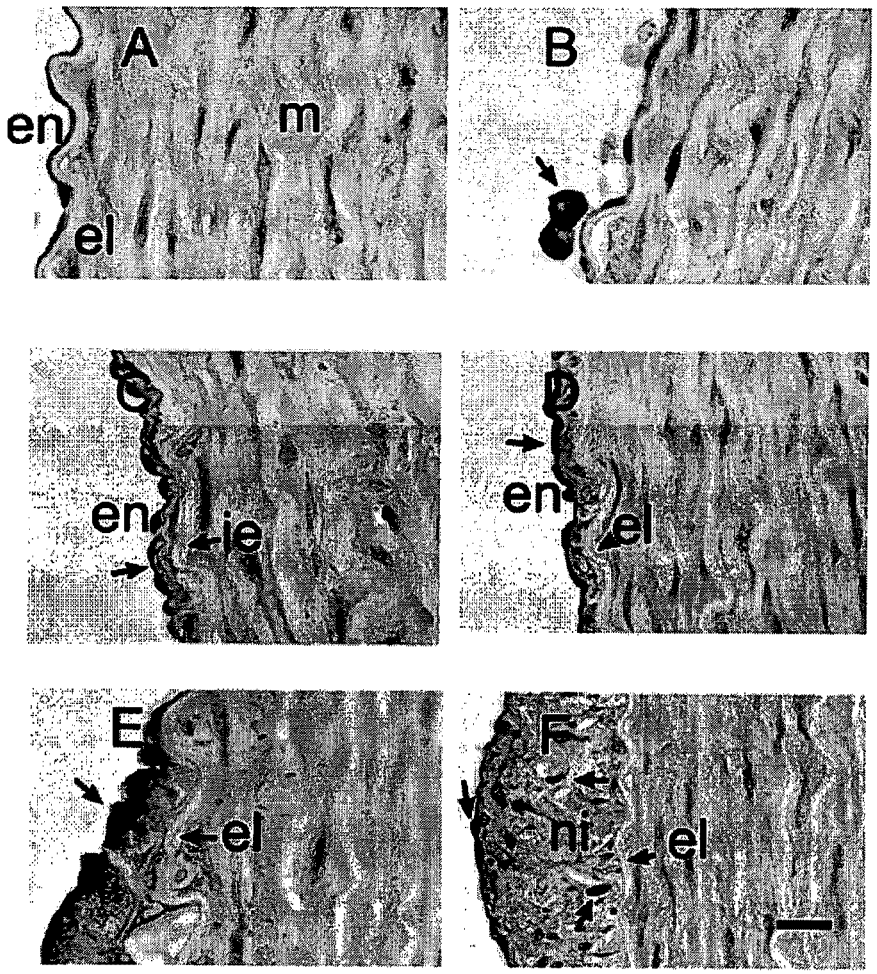

FIG. 5. The thoracic aortas (TA) of control (panels A & B) and diseased (panels C-F, fed 1% methionine and 0.5% cholesterol for 12 weeks) rabbits. In the TA of control rabbits (panels A & B) endothelial cells stained negatively using the monoclonal antibody MAb 31-01. However, CTR-positive, nucleated cells could be found adjacent to the endothelium (as shown in panel B). CTR-positive cells were integrated into the endothelial layer next to the thickened neo-intima (ni) of diseased vessels (panels C-F). CTR-positive cells were also found integrated within atherosclerotic plaque (panel F, arrowed). Abbreviations: el, ie, internal elastic lamina; ni, neo-intima; m, media. Scale bar=20 μm.

Figure 6:
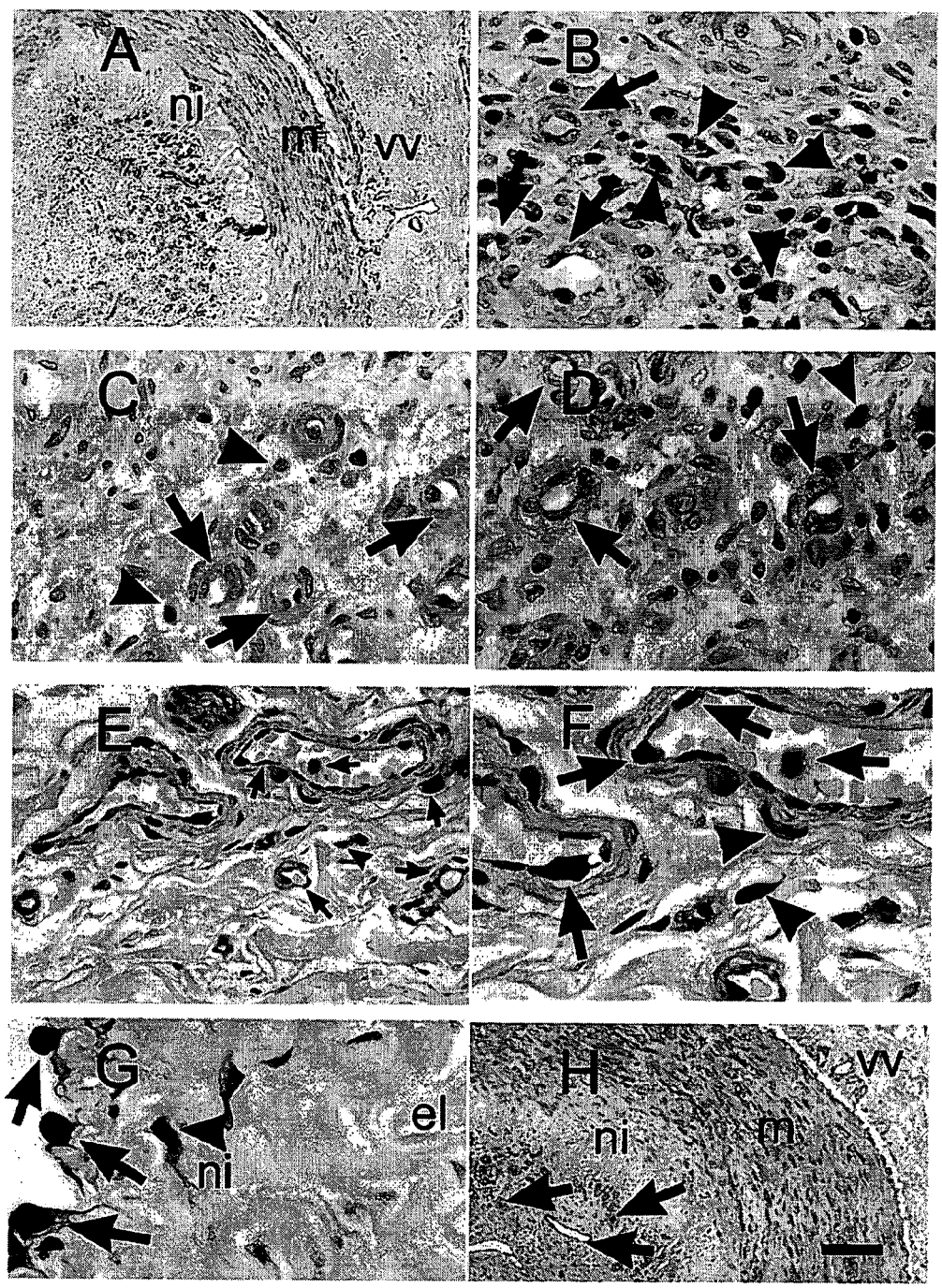

FIG. 6. Shown are images of staining using anti-CTR antibodies and human vessels. In panel A is a view (low magnification) of a diseased radial artery that has ruptured forming a re-canulated thrombis. More highly magnified images are shown in panels B, C & D. Small nascent blood vessels are evident (arrowed in panels B, C & D) in the thrombis and the endothelial cells of these are CTR-positive. Also evident are CTR-positive cells between vessels (arrowheads). Within the vasa vasorum (vv in panel A) the endothelial cells of small vessels and a blood-borne, nucleated cell are also CTR-positive (arrowed in panels E & F) together with unidentified cell types surrounding these vessels (arrowheads). Of particular interest is the CTR-positive, nucleated cell shown with high power in panel F. In panel G, CTR-positive cells were also found in the neo-intima of diseased human internal mammary artery (IMA) as well as cells attached to the endothelial layer (arrows). The images from human radial and internal mammary arteries (panels A-G) were stained using the monoclonal MAb 31-01, whereas panel H was developed with the polyclonal antibody PAb 189/10 (AbD Serotec). Colour was developed with the chromagens diaminobenzidine (DAB) (brown colour, panels A-G) or 3-amino-9-ethylcarbazole (AEC) (red colour, panel H) as described in Zulli et al. (2005). Abbreviations: el, internal elastic layer; ni, neo-intima; m, media; vv, vasa vasorum.

Figure 7:
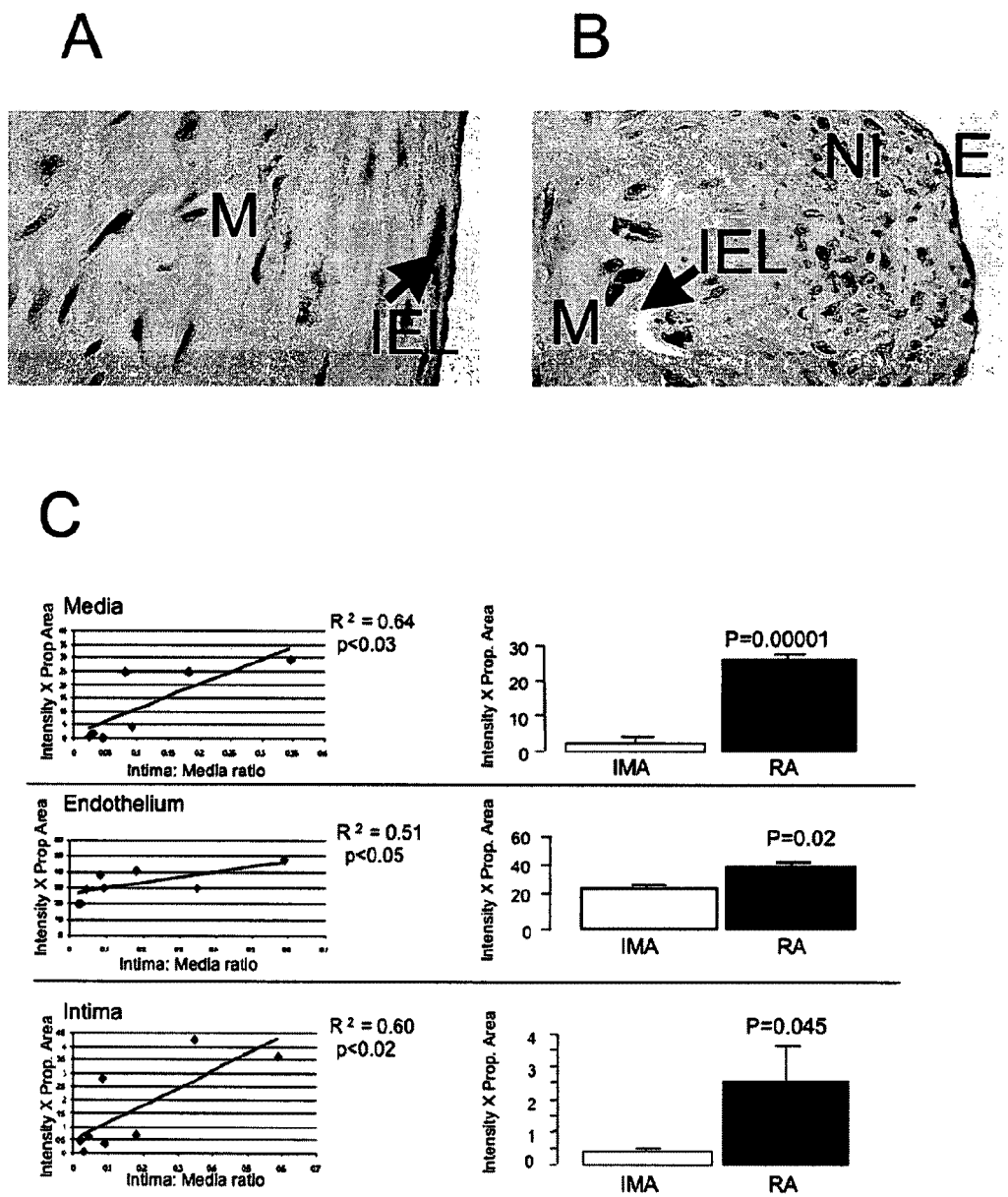

FIG. 7. Shown is an example of CTR expression in a non-diseased section of internal mammary arteries (IMA (A)), in which expression of CTR is minimal, and a representative section of diseased radial arteries (RA (B)). In panel C are shown the graphical representations of the correlations of I×PA for CTR staining versus the ratio of intima/media in the media, intima and endothelium of IMAs and RAs. Also shown are the comparisons of these parameters for the two groups, the IMAs versus RAs. Abbreviations: IEL, internal elastic layer; NI, neo-intima; M, media.

DETAILED DESCRIPTION OF THE INVENTION

Microorganism Deposit Details

The hybridoma designated 1C11 was deposited on 10 Aug. 2007 with the European Collection of Cell Cultures (ECACC) under Deposit Reference 07081002.

The hybridoma designated 9B4 was deposited on 10 Aug. 2007 with the European Collection of Cell Cultures (ECACC) under Deposit Reference 07081001.

These deposits were made under the provisions of the Budapest Treaty on the International Recognition of the Deposit of Microorganisms for the Purpose of Patent Procedure and the Regulations thereunder. This assures maintenance of viable cultures for 30 years from the date of deposit. The organisms will be made available by the ECACC under the terms of the Budapest Treaty which assures permanent and unrestricted availability of the progeny of the culture to the public upon issuance of the pertinent patent.

The assignee of the present application has agreed that if the culture deposit should die or be lost or destroyed when cultivated under suitable conditions, it will be promptly replaced on notification with a viable specimen of the same culture. Availability of a deposited strain is not to be construed as a license to practice the invention in contravention of the rights granted under the authority of any government in accordance with its patent laws.

General Techniques and Definitions

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

As used herein, the term "subject" refers to an animal such as a mammal, e.g. humans or non-human mammals such as cats, dogs, cattle, sheep, horses, rabbits and monkeys. In a preferred embodiment, the subject is a human.

The "sample" may be of any suitable type and may refer, e.g., to a material suspected of containing calcitonin receptor expressing cells. The sample can be used as obtained directly from the source or following at least one step of (partial) purification. The sample can be prepared in any convenient medium which does not interfere with the method of the invention. Typically, the sample is an aqueous solution, biological fluid, cells or tissue. Preferably, the sample is blood, blood vessel and/or bone marrow. The sample can be used as obtained directly from the source or following at least one step of (partial) purification. Pre-treatment may involve, for example, preparing plasma from blood, diluting viscous fluids, and the like. Methods of treatment can involve filtration, distillation, separation, concentration, inactivation of interfering components, and the addition of reagents. The selection and pre-treatment of biological samples prior to testing is well known in the art and need not be described further.

As used herein, the term "blast cell" refers to any precursor cell and includes, for example, multipotential precursor cells and hematopoietic precursor cells. Precursor cells are also referred to as stem cells.

The terms "enriched", "enrichment" or variations thereof are used herein to describe a population of cells in which the proportion of one particular cell type or the proportion of a number of particular cell types is increased when compared with the untreated population.

As used herein the terms "treating", "treat" or "treatment" include administering a therapeutically effective amount of a compound as described herein sufficient to reduce or delay the onset or progression of leukemia, or to reduce or eliminate at least one symptom of cardiovascular disease. In an embodiment, the leukemia to be treated is non-chronic myelogenous leukemia (non-CML). In another embodiment, the leukemia to be treated is acute myelogenous leukemia or acute lymphoblastic leukemia.

The term "preventing" refers to protecting a subject from developing at least one symptom of leukemia or cardiovascular disease, or reducing the severity of a symptom of leukemia or cardiovascular disease.

As used herein, the term "diagnosis", and variants thereof such as, but not limited to, "diagnose", "diagnosed" or "diagnosing" shall not be limited to a primary diagnosis of a clinical state, but should be taken to include any primary diagnosis or prognosis of a clinical state or diagnosis of recurrent disease.

Calcitonin Receptor

CTR is comprised of seven transmembrane domains and is coupled by G-proteins to second messenger systems (Lin et al., 1991). Technologies based on the polymerase chain reaction (PCR) including in situ hybridization, and in vitro autoradiography have been the principal techniques used to demonstrate the widespread expression of CTR mRNA and binding sites within adult tissues. Positive tissues included the kidney, osteoclasts, brain, prostate, skeletal muscle, placenta, primary cells of breast cancer, and related cell lines.

Previously, a physiological function of the thyrocalcitonin (CT)/receptor (CTR) complex had been described in terms of a homeostatic mechanism for calcium, which was active under conditions of hypercalcaemia (Copp et al., 1962; Hirsch and Baruch, 2003; Hirsch et al., 1964). In this model the restricted expression of CTR by osteoclasts and renal tubular epithelial cells plays central roles in the excretion of excess calcium. More recently, a physiological role for CTR in bone metabolism has been refined and described in terms of the regulation of bone formation (Dacquin et al., 2004) rather than bone loss in which amylin/amylin receptor complex plays a role.

In experiments designed to define more precisely the expression of CTRs during development, constructs of the promoter regions of human CTR (Jagger et al., 2000) and porcine CTR (Jagger et al., 1999) have been linked to the reporter gene β-galactosidase and used to create transgenic mice. These studies further emphasized the wide spread expression of CTR in foetal development and raised the prospect of its importance in foetal and postnatal tissue development, and morphogenesis (Jagger et al., 2000). Many of the foetal tissues that express CTR do so beginning early in the second half of gestation, a period characterized by the migration of blast cells that are recruited by different developing organs.

Compounds that Bind CTR

The present inventor has now shown, for the first time, that the calcitonin receptor (CTR) is expressed by cells associated with leukemia. It is envisaged that compounds that bind to CTR will be useful in the diagnosis or detection of leukemia. In addition, antibodies directed against CTR will be capable of killing leukemia cells through mechanisms such as antibody-dependent cell-mediated cytotoxicity (ADCC), complement dependent lysis and apoptosis and will therefore be effective therapeutic agents against leukemia cells. Compounds directed against CTR can also be used to deliver cytotoxins to malignant cells.

The present inventors have also shown that the calcitonin receptor (CTR) is expressed in damaged or diseased tissue associated with, for example, diseases such as cardiovascular disease, and with wound healing. Thus, compounds that bind CTR will be useful in the detection of damaged or diseased tissue and the diagnosis of diseases such as cardiovascular disease. In addition, compounds that bind CTR and which modulate the activity or division of, or life span of CTR expressing cells can be used for treating diseases such as cardiovascular disease, and in particular atherosclerosis. Furthermore, compounds that bind CTR and/or stimulate the activity or proliferation of CTR expressing cells will be useful for stimulating wound healing.

Compounds that bind CTR that are useful in the present invention may be any compound, e.g. a polypeptide, ligand or other molecule, identified as having binding affinity to CTR. The binding between a compound and CTR may be mediated by covalent or non-covalent interactions or a combination of covalent and non-covalent interactions. When the interaction of the compound and CTR produces a non-covalently bound complex, the binding which occurs is typically electrostatic, hydrogen-bonding, or the result of hydrophilic/lipophilic interactions. Particularly preferred compounds that bind CTR are anti-CTR antibodies.

The term "antibody" as used in this invention includes polyclonal antibodies, monoclonal antibodies, bispecific antibodies, diabodies, triabodies, heteroconjugate antibodies, chimeric antibodies including intact molecules as well as fragments thereof, such as Fab, F(ab')2, and Fv which are capable of binding the epitopic determinant, and other antibody-like molecules.

In one embodiment, the disease to be treated is leukemia.

In another embodiment, the disease to be treated is cardiovascular disease. Compounds that bind CTR can also be used to deliver cytotoxins and/or biological response modifiers to CTR expressing cells.

In another embodiment, the compound enhances plaque stability, and hence reduces the risk of rupture and stroke.

Although not essential, the compound may bind specifically to CTR. The phrase "bind specifically," means that under particular conditions, the compound binds CTR and does not bind to a significant amount to other, for example, proteins or carbohydrates. Specific binding to CTR under such conditions may require an antibody that is selected for its specificity. A variety of immunoassay formats may be used to select antibodies specifically immunoreactive with CTR. For example, solid-phase ELISA immunoassays are routinely used to select antibodies specifically immunoreactive with a protein or carbohydrate. See Harlow and Lane (1988) Antibodies, a Laboratory Manual, Cold Spring Harbor Publications, New York, for a description of immunoassay formats and conditions that can be used to determine specific immunoreactivity.

As used herein "binds an epitope" means that an antibody need only bind within the given amino acid sequence, and need not bind the entire amino acid sequence.

Anti-CTR antibodies will be known to those skilled in the art and have been used to detect CTR expression in certain tissues. CTR has not been used to date, however, as a target for the treatment of leukemia or cardiovascular disease, or for the detection or localization of CTR expressing cell in leukemia, cardiovascular disease or during wound healing. Examples of suitable anti-CTR antibodies include MCA2191 (AbD Serotec, UK), ab1102 (Abcam, UK), Pab 189 (AHP 635; AbD Serotec, UK), MCA 2122 (AbD Serotec, UK) and MCA 2192 (AbD Serotec, UK).

Anti-CTR antibodies that have been developed by the present inventors include MAb 1C11 (produced by the hybridoma deposited with the ECACC under Deposit Reference 07081002) and MAb 9B4 (produced by the hybridoma deposited with the ECACC under Deposit Reference 07081001). The monoclonal antibodies 1C11 and 9B4 recognize a CTR epitope having the amino acid sequence of SEQ ID NO: 5.

Antibodies may exist as intact immunoglobulins, or as modifications in a variety of forms including, for example, but not limited to, domain antibodies including either the VH or VL domain, a dimer of the heavy chain variable region (VHH, as described for a camelid), a dimer of the light chain variable region (VLL), Fv fragments containing only the light and heavy chain variable regions, or Fd fragments containing the heavy chain variable region and the CH1 domain. A scFv consisting of the variable regions of the heavy and light chains linked together to form a single-chain antibody (Bird et al., 1988; Huston et al., 1988) and oligomers of scFvs such as diabodies and triabodies are also encompassed by the term "antibody". Also encompassed are fragments of antibodies such as Fab, (Fab')$_2$ and FabFc$_2$ fragments which contain the variable regions and parts of the constant regions. Complementarity determining region (CDR)-grafted antibody fragments and oligomers of antibody fragments are also encompassed. The heavy and light chain components of an Fv may be derived from the same antibody or different antibodies thereby producing a chimeric Fv region. The antibody may be of animal (for example mouse, rabbit or rat) or human origin or may be chimeric (Morrison et al., 1984) or humanized (Jones et al., 1986), and published UK patent application No. 8707252. As used herein the term "antibody" includes these various forms. Using the guidelines provided herein and those methods well known to those skilled in the art which are described in the references cited above and in such publications as Harlow & Lane, Antibodies: a Laboratory Manual, Cold Spring Harbor Laboratory, (1988) the antibodies for use in the methods of the present invention can be readily made.

The CTR-binding antibodies may be Fv regions comprising a variable light ($V_L$) and a variable heavy ($V_H$) chain. The light and heavy chains may be joined directly or through a linker. As used herein a linker refers to a molecule that is covalently linked to the light and heavy chain and provides enough spacing and flexibility between the two chains such that they are able to achieve a conformation in which they are capable of specifically binding the epitope to which they are directed. Protein linkers are particularly preferred as they may be expressed as an intrinsic component of the Ig portion of the fusion polypeptide.

In another embodiment, recombinantly produced single chain scFv antibody, preferably a humanized scFv, is used in the methods of the invention.

Monoclonal Antibodies

Monoclonal antibodies directed against CTR epitopes can be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against CTR epitopes can be screened for various properties; i.e. for isotype and epitope affinity.

Animal-derived monoclonal antibodies can be used for both direct in vivo and extracorporeal immunotherapy. However, it has been observed that when, for example, mouse-derived monoclonal antibodies are used in humans as therapeutic agents, the patient produces human anti-mouse antibodies. Thus, animal-derived monoclonal antibodies are not preferred for therapy, especially for long term use. With established genetic engineering techniques it is possible, however, to create chimeric or humanized antibodies that have animal-derived and human-derived portions. The animal can be, for example, a mouse or other rodent such as a rat.

If the variable region of the chimeric antibody is, for example, mouse-derived while the constant region is human-derived, the chimeric antibody will generally be less immunogenic than a "pure" mouse-derived monoclonal antibody. These chimeric antibodies would likely be more suited for therapeutic use, should it turn out that "pure" mouse-derived antibodies are unsuitable.

Methodologies for generating chimeric antibodies are available to those in the art. For example, the light and heavy chains can be expressed separately, using, for example, immunoglobulin light chain and immunoglobulin heavy chains in separate plasmids. These can then be purified and assembled in vitro into complete antibodies; methodologies for accomplishing such assembly have been described (see, for example, Sun et al., 1986). Such a DNA construct may comprise DNA encoding functionally rearranged genes for the variable region of a light or heavy chain of an anti-CTR antibody linked to DNA encoding a human constant region. Lymphoid cells such as myelomas or hybridomas transfected with the DNA constructs for light and heavy chain can express and assemble the antibody chains.

In vitro reaction parameters for the formation of IgG antibodies from reduced isolated light and heavy chains have also been described (see, for example, Beychok, 1979). Co-expression of light and heavy chains in the same cells to achieve intracellular association and linkage of heavy and light chains into complete H2L2 IgG antibodies is also possible. Such co-expression can be accomplished using either the same or different plasmids in the same host cell.

Humanising Methodologies/Techniques

In another preferred embodiment of the present invention the anti-CTR antibody is humanized, that is, an antibody produced by molecular modeling techniques wherein the human content of the antibody is maximised while causing little or no loss of binding affinity attributable to the variable region of, for example, a parental rat, rabbit or murine antibody.

An antibody may be humanized by grafting the desired CDRs onto a human framework according to EP-A-0239400. A DNA sequence encoding the desired reshaped antibody can therefore be made beginning with the human DNA whose CDRs it is wished to reshape. The animal-derived variable domain amino acid sequence containing the desired CDRs is compared to that of the chosen human antibody variable domain sequence. The residues in the human variable domain are marked that need to be changed to the corresponding residue in the animal to make the human variable region incorporate the animal-derived CDRs. There may also be residues that need substituting in, adding to or deleting from the human sequence.

Oligonucleotides are synthesized that can be used to mutagenize the human variable domain framework to contain the desired residues. Those oligonucleotides can be of any convenient size. One is normally only limited in length by the capabilities of the particular synthesizer one has available. The method of oligonucleotide-directed in vitro mutagenesis is well known.

Alternatively, humanisation may be achieved using the recombinant polymerase chain reaction (PCR) methodology of WO 92/07075. Using this methodology, a CDR may be spliced between the framework regions of a human antibody. In general, the technique of WO 92/07075 can be performed using a template comprising two human framework regions, AB and CD, and between them, the CDR which is to be replaced by a donor CDR. Primers A and B are used to amplify the framework region AB, and primers C and D used to amplify the framework region CD. However, the primers B and C each also contain, at their 5' ends, an additional sequence corresponding to all or at least part of the donor CDR sequence. Primers B and C overlap by a length sufficient to permit annealing of their 5' ends to each other under conditions which allow a PCR to be performed. Thus, the amplified regions AB and CD may undergo gene splicing by overlap extension to produce the humanized product in a single reaction.

Following the mutagenesis reactions to reshape the antibody, the mutagenised DNAs can be linked to an appropriate DNA encoding a light or heavy chain constant region, cloned into an expression vector, and transfected into host cells, preferably mammalian cells. These steps can be carried out in routine fashion. A reshaped antibody may therefore be prepared by a process comprising:

(a) preparing a first replicable expression vector including a suitable promoter operably linked to a DNA sequence which encodes at least a variable domain of an Ig heavy or light chain, the variable domain comprising framework regions from a human antibody and the CDRs required for the humanized antibody of the invention;

(b) preparing a second replicable expression vector including a suitable promoter operably linked to a DNA sequence which encodes at least the variable domain of a complementary Ig light or heavy chain respectively;

(c) transforming a cell line with the first or both prepared vectors; and (d) culturing said transformed cell line to produce said altered antibody.

Preferably the DNA sequence in step (a) encodes both the variable domain and each constant domain of the human antibody chain. The humanized antibody can be prepared using any suitable recombinant expression system. The cell line which is transformed to produce the altered antibody may be a Chinese Hamster Ovary (CHO) cell line or an immortalised mammalian cell line, which is advantageously of lymphoid origin, such as a myeloma, hybridoma, trioma or quadroma cell line. The cell line may also comprise a normal lymphoid cell, such as a B-cell, which has been immortalised by transformation with a virus, such as the Epstein-Barr virus. Most preferably, the immortalised cell line is a myeloma cell line or a derivative thereof.

The CHO cells used for expression of the antibodies may be dihydrofolate reductase (dhfr) deficient and so dependent on thymidine and hypoxanthine for growth (Urlaub and Chasin, 1980). The parental dhfr⁻ CHO cell line is transfected with the DNA encoding the antibody and dhfr gene which enables selection of CHO cell transformants of dhfr positive phenotype. Selection is carried out by culturing the colonies on media devoid of thymidine and hypoxanthine, the absence of which prevents untransformed cells from growing and transformed cells from resalvaging the folate pathway and thus bypassing the selection system. These transformants usually express low levels of the DNA of interest by virtue of co-integration of transfected DNA of interest and DNA encoding dhfr. The expression levels of the DNA encoding the antibody may be increased by amplification using methotrexate (MTX). This drug is a direct inhibitor of the enzyme dhfr and allows isolation of resistant colonies which amplify their dhfr gene copy number sufficiently to survive under these conditions. Since the DNA sequences encoding dhfr and the antibody are closely linked in the original transformants, there is usually concomitant amplification, and therefore increased expression of the desired antibody.

Another preferred expression system for use with CHO or myeloma cells is the glutamine synthetase (GS) amplification system described in WO 87/04462. This system involves the transfection of a cell with DNA encoding the enzyme GS and with DNA encoding the desired antibody. Cells are then selected which grow in glutamine free medium and can thus be assumed to have integrated the DNA encoding GS. These selected clones are then subjected to inhibition of the enzyme GS using methionine sulphoximine (Msx). The cells, in order to survive, will amplify the DNA encoding GS with concomitant amplification of the DNA encoding the antibody.

Although the cell line used to produce the humanized antibody is preferably a mammalian cell line, any other suitable cell line, such as a bacterial cell line or a yeast cell line, may alternatively be used. In particular, it is envisaged that *E. coli*-derived bacterial strains could be used. The antibody obtained is checked for functionality. If functionality is lost, it is necessary to return to step (2) and alter the framework of the antibody.

Once expressed, the whole antibodies, their dimers, individual light and heavy chains, or other immunoglobulin forms can be recovered and purified according to standard procedures of the art, including ammonium sulfate precipitation, affinity columns, column chromatography, gel electrophoresis and the like (See, generally, Scopes, R., Protein Purification, Springer-Verlag, N.Y. (1982)). Substantially pure immunoglobulins of at least about 90 to 95% homogeneity are preferred, and 98 to 99% or more homogeneity most preferred, for pharmaceutical uses. Once purified, partially or to homogeneity as desired, a humanized antibody may then be used therapeutically or in developing and performing assay procedures, immunofluorescent stainings, and the like (See, generally, Immunological Methods, Vols. I and II, Lefkovits and Pernis, eds., Academic Press, New York, N.Y. (1979 and 1981)).

Studies carried out by Greenwood et al. (1993) have demonstrated that recognition of the Fc region of an antibody by human effector cells can be optimised by engineering the constant region of the immunoglobulin molecule. This could be achieved by fusing the variable region genes of the antibody, with the desired specificity, to human constant region genes encoding immunoglobulin isotypes that have demonstrated effective ADCC in human subjects, for example the IgG1 and IgG3 isotypes (Greenwood and Clark (1993) Protein Engineering of Antibody Molecules for Prophylactic and Therapeutic Applications in Man. Edited by Mike Clark, published by Academic Titles. Section II 85-113). The resulting chimeric or humanized antibodies to CTR should be particularly effective in inducing ADCC.

Antibodies with fully human variable regions against CTR can also be prepared by administering the antigen to a transgenic animal which has been modified to produce such antibodies in response to antigenic challenge, but whose endogenous loci have been disabled. Various subsequent manipulations can be performed to obtain either antibodies per se or analogs thereof (see, for example, U.S. Pat. No. 6,075,181).

Preparation of Genes Encoding Antibodies or Fragments Thereof

Genes encoding antibodies, both light and heavy chain genes or portions thereof, e.g., single chain Fv regions, may be cloned from a hybridoma cell line. They may all be cloned using the same general strategy. Typically, for example, poly (A)$^+$ mRNA extracted from the hybridoma cells is reverse transcribed using random hexamers as primers. For Fv regions, the $V_H$ and $V_L$ domains are amplified separately by two polymerase chain reactions (PCR). Heavy chain sequences may be amplified using 5' end primers which are designed according to the amino-terminal protein sequences of the anti-CTR heavy chains respectively and 3' end primers according to consensus immunoglobulin constant region sequences (Kabat et al., Sequences of Proteins of Immunological Interest. 5th edition. U.S. Department of Health and Human Services, Public Health Service, National Institutes of Health, Bethesda, Md. (1991). Light chain Fv regions are amplified using 5' end primers designed according to the amino-terminal protein sequences of anti-CTR light chains and in combination with the primer C-kappa. One of skill in the art would recognize that many suitable primers may be employed to obtain Fv regions.

The PCR products are subcloned into a suitable cloning vector. Clones containing the correct size insert by DNA restriction are identified. The nucleotide sequence of the heavy or light chain coding regions may then be determined from double stranded plasmid DNA using sequencing primers adjacent to the cloning site. Commercially available kits (e.g., the Sequenase™ kit, United States Biochemical Corp., Cleveland, Ohio, USA) may be used to facilitate sequencing the DNA. DNA encoding the Fv regions may be prepared by any suitable method, including, for example, amplification techniques such as PCR and LCR.

Chemical synthesis produces a single stranded oligonucleotide. This may be converted into double stranded DNA by hybridization with a complementary sequence, or by polymerization with a DNA polymerase using the single strand as a template. While it is possible to chemically synthesize an entire single chain Fv region, it is preferable to synthesize a number of shorter sequences (about 100 to 150 bases) that are later ligated together.

Alternatively, sub-sequences may be cloned and the appropriate subsequences cleaved using appropriate restriction enzymes. The fragments may then be ligated to produce the desired DNA sequence.

Once the Fv variable light and heavy chain DNA is obtained, the sequences may be ligated together, either directly or through a DNA sequence encoding a peptide linker, using techniques well known to those of skill in the art. In one embodiment, heavy and light chain regions are connected by a flexible peptide linker (e.g., $(Gly_4Ser)_3$) which starts at the carboxyl end of the heavy chain Fv domain and ends at the amino terminus of the light chain Fv domain. The entire sequence encodes the Fv domain in the form of a single-chain antigen binding protein.

Diagnosis or Prognosis of Disease and Detecting Damaged Tissue

Leukemia (or leukaemia) is a cancer of the blood or bone marrow characterized by an abnormal proliferation of blood cells, usually white blood cells (leukocytes). The are four main types of leukemia; acute myelogenous leukemia (AML), acute lymphocytic leukemia (ALL), chromic myelogenous leukemia (CML) and chronic lymphocytic leukemia (CLL), and other subsets of the disease, for example, hairy cell leukemia.

As used herein, the term "leukemia cell" refers to an abnormal blood cell that has an inability to carry out the functions of healthy blood cells. The term "leukemia cell" includes immature blood cells, referred to as "blasts" or "precursors".

The term "hematopoietic precursor" includes hematopoietic stem cells, hematopoietic progenitor cells or any cell which gives rise to a cell in the hematopoietic lineages (e.g., lymphoid, myeloid).

In one embodiment, the present invention provides a method of diagnosing leukemia or a predisposition to leukemia in a subject, the method comprising determining the presence or level of expression of CTR in a sample obtained from the subject, wherein the presence or an increased level of expression of CTR is indicative of leukemia.

The sample used in the methods of the present invention may be any sample that comprises leukemia cells. For example, the sample may comprise blood or bone marrow cells.

Compounds that bind CTR can also be used to detect diseased and damaged tissue. For example, the compound may be used in methods for imaging an internal region of a subject and/or diagnosing the presence or absence of a disease in a subject. For example, compounds that bind CTR can be used for the diagnosis of diseases in which CTR expressing cells play a role. An example of a disease in which CTR expressing cells play a role is cardiovascular disease.

It will be apparent from the preceding description that the diagnostic or prognostic methods of the present invention involve a degree of quantification to determine levels of CTR present in patient samples. Such quantification is readily provided by the inclusion of appropriate control samples.

Preferably, internal controls are included in the methods of the present invention. A preferred internal control is one or more samples taken from one or more healthy individuals.

In the present context, the term "healthy individual" shall be taken to mean an individual who is known not to suffer from leukemia or cardiovascular disease, such knowledge being derived from clinical data on the individual, including, but not limited to, a different diagnostic assay to that described herein.

As will be known to those skilled in the art, when internal controls are not included in each assay conducted, the control may be derived from an established data set.

Data pertaining to the control subjects are preferably selected from the group consisting of:

1. a data set comprising measurements of the presence or level of expression of CTR for a typical population of subjects known to have leukemia or cardiovascular disease;

2. a data set comprising measurements of the presence or level of expression of CTR for the subject being tested wherein said measurements have been made previously, such as, for example, when the subject was known to be healthy or, in the case of a subject having leukemia or cardiovascular disease, when the subject was diagnosed or at an earlier stage in disease progression;

3. a data set comprising measurements of the presence or level of expression of CTR for a healthy individual or a population of healthy individuals; and 4. a data set comprising measurements of the presence or level of expression of CTR for a normal individual or a population of normal individuals.

In the present context, the term "typical population" with respect to subjects known to have leukemia or cardiovascular disease shall be taken to refer to a population or sample of subjects diagnosed with leukemia or cardiovascular disease that is representative of the spectrum of leukemia or cardiovascular disease patients. This is not to be taken as requiring a strict normal distribution of morphological or clinicopathological parameters in the population, since some variation in such a distribution is permissible. Preferably, a "typical population" will exhibit a spectrum of leukemia or cardiovascular diseases at different stages of disease progression. It is particularly preferred that a "typical population" exhibits the expression characteristics of a cohort of subjects as described herein.

The term "normal individual" shall be taken to mean an individual that does not express CTR, or expresses CTR at a low level, in a leukocyte or blood precursor cell, or in blood vessel tissue. As will be known to those skilled in the art, data obtained from a sufficiently large sample of the population will normalize, allowing the generation of a data set for determining the average level of a particular marker.

Those skilled in the art are readily capable of determining the baseline for comparison in any diagnostic assay of the present invention without undue experimentation, based upon the teaching provided herein.

Compounds that bind CTR when used diagnostically may be linked to a diagnostic reagent such as a detectable label to allow easy detection of binding events in vitro or in vivo. Suitable labels include radioisotopes, dye markers or other imaging reagents for detection and/or localisation of target molecules. Compounds linked to a detectable label can be used with suitable in vivo imaging technologies such as, for example, radiology, fluoroscopy, nuclear magnetic resonance imaging (MRI), CAT-scanning, positron emission tomography (PET), computerized tomography etc.

By way of non-limiting example, the CTR compounds coupled to imaging agents can be used in the detection of CTR expression in histochemical tissue sections. The compound may be covalently or non-covalently coupled to a suitable supermagnetic, paramagnetic, electron dense, echogenic, radioactive, or non-radioactive labels such as biotin or avidin.

Protein Detection Techniques

In one embodiment, a protein or an immunogenic fragment or epitope of CTR is detected in a patient sample, wherein the level and/or timing of production of the protein or immunogenic fragment or epitope in the sample is indicative of leukemia or cardiovascular disease. Preferably, the method comprises contacting a biological sample derived from the subject with an antibody capable of binding to CTR or an immunogenic fragment or epitope thereof, and detecting the formation of an antigen-antibody complex.

In another embodiment, an antibody against CTR or epitope thereof is detected in a patient sample, wherein the level and/or timing of production of the antibody in the sample is indicative of leukemia or cardiovascular disease. Preferably, the method comprises contacting a biological sample derived from the subject with CTR or an antigenic fragment e.g., a B cell epitope or other immunogenic fragment thereof, and detecting the formation of an antigen-antibody complex.

Preferred detection systems contemplated herein include any known assay for detecting proteins or antibodies in a biological sample isolated from a human subject, such as, for example, SDS/PAGE, isoelectric focussing, 2-dimensional gel electrophoresis comprising SDS/PAGE and isoelectric focussing, an immunoassay, flow cytometry e.g. fluorescence-activated cell sorting (FACS), a detection based system using an antibody or non-antibody compound, such as, for example, a small molecule (e.g. a chemical compound, agonist, antagonist, allosteric modulator, competitive inhibitor, or non-competitive inhibitor, of the protein). In accordance with these embodiments, the antibody or small molecule may be used in any standard solid phase or solution phase assay format amenable to the detection of proteins. Optical or fluorescent detection, such as, for example, using mass spectrometry, MALDI-TOF, biosensor technology, evanescent fiber optics, or fluorescence resonance energy transfer, is clearly encompassed by the present invention. Assay systems suitable for use in high throughput screening of mass samples, e.g. a high throughput spectroscopy resonance method (e.g. MALDI-TOF, electrospray MS or nano-electrospray MS), are also contemplated.

Immunoassay formats are particularly suitable, e.g., selected from the group consisting of, an immunoblot, a Western blot, a dot blot, an enzyme linked immunosorbent assay (ELISA), radioimmunoassay (RIA), enzyme immunoassay. Modified immunoassays utilizing fluorescence resonance energy transfer (FRET), isotope-coded affinity tags (ICAT), matrix-assisted laser desorption/ionization time of flight (MALDI-TOF), electrospray ionization (ESI), biosensor technology, evanescent fiber-optics technology or protein chip technology are also useful.

Preferably, the assay is a semi-quantitative assay or quantitative assay.

Standard solid phase ELISA formats are particularly useful in determining the concentration of a protein or antibody from a variety of patient samples.

In one form, such an assay involves immobilising a biological sample comprising antibodies against CTR or an immunogenic fragment thereof, onto a solid matrix, such as, for example a polystyrene or polycarbonate microwell or dipstick, a membrane, or a glass support (e.g. a glass slide).

In the case of an antigen-based assay, an antibody that specifically binds CTR is brought into direct contact with the immobilised biological sample, and forms a direct bond with any of its target protein present in said sample. For an antibody-based assay, immobilized CTR or an immunogenic fragment or epitope thereof is contacted with the sample. The added antibody or protein in solution is generally labelled with a detectable reporter molecule, such as for example, a fluorescent label (e.g. FITC or Texas Red) or an enzyme (e.g. horseradish peroxidase (HRP)), alkaline phosphatase (AP) or β-galactosidase. Alternatively, or in addition, a second labelled antibody can be used that binds to the first antibody or to the isolated/recombinant antigen. Following washing to remove any unbound antibody or antigen, as appropriate, the label is detected either directly, in the case of a fluorescent label, or through the addition of a substrate, such as for example hydrogen peroxide, TMB, or toluidine, or 5-bromo-4-chloro-3-indol-beta-D-galaotopyranoside (x-gal).

Such ELISA based systems are particularly suitable for quantification of the amount of a protein or antibody in a sample, such as, for example, by calibrating the detection system against known amounts of a standard.

In another form, an ELISA consists of immobilizing an antibody that specifically binds CTR on a solid matrix, such as, for example, a membrane, a polystyrene or polycarbonate microwell, a polystyrene or polycarbonate dipstick or a glass support. A patient sample is then brought into physical relation with said antibody, and the antigen in the sample is bound or 'captured'. The bound protein can then be detected using a labelled antibody. For example if the protein is captured from a human sample, an anti-human antibody is used to detect the captured protein. Alternatively, a third labelled antibody can be used that binds the second (detecting) antibody.

Nucleic Acid Detection Techniques

Any suitable technique that allows for the qualitative and/or quantitative assessment of the level of expression of a specific gene in a tissue may be used. Comparison may be made by reference to a standard control, or to a control level that is found in healthy tissue. For example, levels of a transcribed gene can be determined by Northern blotting, and/or RT-PCR. With the advent of quantitative (real-time) PCR, quantitative analysis of gene expression can be achieved by using appropriate primers for the gene of interest. The nucleic acid may be labelled and hybridised on a gene array, in which case the gene concentration will be directly proportional to the intensity of the radioactive or fluorescent signal generated in the array.

In one particular example, leukemia or cardiovascular disease may be diagnosed by contacting nucleic acid isolated from patient samples with a nucleic acid probe under stringent hybridisation conditions that allow the formation of a hybrid complex between the nucleic acid probe and the gene encoding CTR (SEQ ID NO: 1) and detecting the presence of a hybrid complex in the samples. For use as a diagnostic agent, it may be preferable to label the nucleic acid probe to aid its detection. This level of detection is compared to control levels, such as, for example, gene levels from a healthy specimen or a standard control; detection of altered levels of the hybrid complex from the patient tissue is indicative of leukemia or cardiovascular disease.

The term "hybridization" as used here refers to the association of two nucleic acid molecules with one another by hydrogen bonding. Factors that affect this bonding include: the type and volume of solvent; reaction temperature; time of hybridization; agitation; agents to block the non-specific attachment of the liquid phase molecule to the solid support (Denhardt's reagent or BLOTTO); the concentration of the molecules; use of compounds to increase the rate of association of molecules (dextran sulphate or polyethylene glycol); and the stringency of the washing conditions following hybridization (see Sambrook et al. Molecular Cloning; A Laboratory Manual, Second Edition (1989)). In accordance with these principles, the inhibition of hybridization of a complementary molecule to a target molecule may be examined using a hybridization assay; a substantially homologous molecule possessing a greater degree of homology will then compete for and inhibit the binding of a completely homologous molecule to the target molecule under various conditions of stringency, as taught in Wahl and Berger (1987) and Kimmel (1987).

"Stringency" refers to conditions in a hybridization reaction that favour the association of very similar molecules over association of molecules that differ. High stringency hybridisation conditions are defined as overnight incubation at 42° C. in a solution comprising 50% formamide, 5×SSC (150 mM NaCl, 15 mM trisodium citrate, pH8.0), 50 mM sodium phosphate (pH7.6), 5×Denhardt's solution, 10% dextran sulphate, and 20 microgram/ml denatured, sheared salmon sperm DNA, followed by washing the filters in 0.1×SSC at approximately 65° C. Low stringency conditions involve the hybridisation reaction being carried out at 35° C. Preferably, the conditions used for hybridization in the methods of the present invention are those of high stringency.

The nucleic acid is preferably separated from the sample for testing. Suitable methods will be known to those of skill in the art. For example, RNA may be isolated from a blood sample to be analysed using conventional procedures, such as are supplied by QIAGEN technology. This RNA is then reverse-transcribed into DNA using reverse transcriptase and the DNA molecule of interest may then be amplified by PCR techniques using specific primers.

Diagnostic procedures may also be performed directly upon patient samples. Hybridisation or amplification assays, such as, for example, Southern or Northern blot analysis, immunohistochemistry, single-stranded conformational polymorphism analysis (SSCP) and PCR analyses are among techniques that are useful in this respect. If desired, target or probe nucleic acid may be immobilised to a solid support such as a microtitre plate, membrane, polystyrene bead, glass slide or other solid phase.

Therapeutic Methods

In one aspect, the present invention utilizes the compounds without modification, relying on the binding of the compounds to CTR expressing cells in situ to stimulate an immune attack thereon. For example, a chimeric antibody, wherein the antigen-binding site is joined to human Fc region, e.g., IgG1, may be used to promote antibody-dependent mediated cytotoxicity or complement-mediated cytotoxicity.

In another aspect of the invention, the therapeutic method may be carried out using compounds that bind CTR to which a cytotoxic agent or biological response modifier is bound. Binding of the resulting conjugate to the CTR expressing cells inhibits the growth of or kills the cells, or modulates the activity, division of, or lifespan of the cells.

A "biological response modifier" refers to any compound, particularly a polypeptide or peptide, that is able to modify, either directly or indirectly, a biological response to a calcitonin receptor expressing cell. By modifying a biological response, the activity, or division of, calcitonin receptor expressing cells is modified, or calcitonin receptor expressing cells are killed.

"Biological response modifiers" include, but are not limited to, lymphokines and cytokines (e.g., interferon gamma (IFNγ), interleukin-1 (IL-1), interleukin-2 (IL-2), interleukin-5 (IL-5), interleukin-6 (IL-6), interleukin-7 (IL-7), interleukin-10 (IL-10), interleukin-12 (IL-12), interleukin-15 (IL-15), interleukin-23 (IL-23), granulocyte macrophage colony stimulating factor (GM-CSF), and granulocyte colony stimulating factor (G-CSF)), or a growth factor (e.g., growth hormone (GH)).

Biological response modifiers may have a variety of effects on CTR expressing cells. Among these effects are increased cell killing by direct action as well as increased cell killing by increased host defense mediated processes. For example, conjugation of a compound that binds CTR to these biological response modifiers will allow selective localization within leukemia cells and, hence, improved anti-proliferative effects while suppressing non-specific effects leading to toxicity of non-target cells.

In the area of leukemia, the antibodies or antibody fragments of the present invention have further utility in the preparation of cellular samples from which leukemia cells have been removed. This use is particularly important in autologous bone marrow transplants, wherein a sample of bone marrow is harvested from a cancer patient prior to the patient's undergoing high-dose chemotherapy. The goal of the high dose chemotherapy is to destroy the cancer cells, which also results in the depletion of bone marrow cells.

Following such treatment, the harvested bone marrow cells are reintroduced into the patient.

In leukemia, the harvested bone marrow is contaminated with leukemia cells; thus, reintroduction of untreated bone marrow will simply reintroduce the disease. Previous methods to prevent reintroduction of cancer cells have included treatment of the bone marrow sample with chemotherapeutic agents and other anti-neoplastic agents in vitro. Other methods include purging the sample of cancer cells.

Thus, in a further practice of the present invention, the compounds described herein may be used to remove leukemia cells from a patient's bone marrow sample before reintroduction into the patient. In one non-limiting example, the compounds are attached to a matrix, such as beads. This may be accomplished by any of several well-known methods for preparing an affinity matrix comprising, for example, antibodies or their binding fragments. The bone marrow sample is then exposed to the matrix, such as by passage of the cells over a column containing the matrix, under conditions to promote the binding of the leukemia cells in the sample through antigen/antibody interactions with the antibodies or binding fragments attached to the matrix. The leukemia cells in the sample adhere to the matrix; while the column effluent, i.e., the non-adherent cellular population, is depleted of leukemia cells. The effectiveness of the procedure may be monitored by examining the cells for residual leukemia cells, such as by using a detectably-labeled antibody as described below. The procedure may be repeated or modified to increase effectiveness.

The aforementioned purging procedure (see, e.g., Ramsay and Kersey, 1988) may be performed with other methods for removing or killing cancer cells, including, but not limited to, exposing the purified bone marrow cells to chemotherapeutic agents. Such chemotherapeutic agents include the use of compounds conjugated to a cytotoxic agent for in vivo therapeutic treatment. Accordingly, conjugates of the compounds with cytotoxic agents may be used for the ex vivo killing of leukemia cells in a cellular sample. The methods may additionally include exposing the cells to cytokines (e.g., GM-CSF, IL-6), cytokine receptors (e.g., IL-6-receptor), mitogens (e.g., poke weed mitogen (PWM)), or adhesion molecules (e.g., CD40 ligand) in order to stimulate the leukemia cells to rapidly differentiate and thereby upregulate expression of cancer-specific antigens on their cell surface. These treatment modalities are intended to render the leukemia cells vulnerable to the in vitro-mediated cytotoxicity achieved by incubation with compound.

In another aspect of the therapeutic methods of the present invention, the compounds conjugated with cytotoxic agents, such as chemotherapeutic agents, a photo-activatable toxin, or a radionuclide, may be used in vitro or ex vivo to inhibit or kill leukemia cells from a patient sample, in the absence of the purging technique described above. The treatment of a sample with the cytotoxic compound conjugates may be combined with other methods to kill cancer cells to increase the effectiveness of a bone marrow transplant, particularly an autologous bone marrow transplant, by removing cells from the tissue to be transplanted. These methods may include additionally exposing the cells to cytokines, etc. Thus, a method is described herein for removing leukemia cells from an isolated cellular sample comprising the steps of exposing the cellular sample to a solid matrix on which a compound is bound under conditions in which the leukemia cells adhere to the compound and isolating a cellular fraction of the cellular sample which does not bind to the matrix. By way of non-limiting example, bone marrow cells are used, particularly for a transplant, and preferably, an autologous bone marrow transplant.

Cytotoxic Agents

A "cytotoxic agent" is any agent that is capable of modulating the activity, or division of, or which kills calcitonin receptor expressing cells. Suitable cytotoxic agents for use in the present invention include, but are not limited to, agents such as bacterial or plant toxins, drugs, e.g., cyclophosphamide (CTX; cytoxan), chlorambucil (CHL; leukeran), cisplatin (CisP; CDDP; platinol), busulfan (myleran), melphalan, carmustine (BCNU), streptozotocin, triethylenemelamine (TEM), mitomycin C, and other alkylating agents; methotrexate (MTX), etoposide (VP-16; vepesid), 6-mercaptopurine (6 MP), 6-thioguanine (6TG), cytarabine (Ara-C), 5-fluorouracil (5FU), dacarbazine (DTIC), 2-chlorodeoxyadenosine (2-CdA), and other antimetabolites; antibiotics including actinomycin D, doxorubicin (DXR; adriamycin), daunorubicin (daunomycin), bleomycin, mithramycin as well as other antibiotics; alkaloids such as vincristin (VCR), vinblastine, and the like; as well as other anti-cancer agents including the cytostatic agents glucocorticoids such as dexamethasone (DEX; decadron) and corticosteroids such as prednisone, nucleotide enzyme inhibitors such as hydroxyurea, and the like.

Those skilled in the art will realize that there are numerous other radioisotopes and chemocytotoxic agents that can be coupled to compounds that bind CTR by well known techniques, and delivered to destroy CTR expressing cells and/or cells in close proximity thereto. In one embodiment, the agents specifically destroy leukemia cells (see, e.g., U.S. Pat. No. 4,542,225). Examples of photo-activated toxins include dihydropyridine- and omega-conotoxin (Schmidt et al., 1991). Examples of cytotoxic reagents that can be used include $^{125}I$, $^{131}I$, $^{111}In$, $^{123}I$, $^{99}mTc$, and $^{32}P$. The antibody can be labeled with such reagents using techniques known in the art. For example, see Wenzel and Meares, Radioimmunoimaging and Radioimmunotherapy, Elsevier, N.Y. (1983) for techniques relating to the radiolabeling of antibodies (see also, Colcher et al., 1986; "Order, Analysis, Results and Future Prospective of the Therapeutic Use of Radiolabeled Antibody in Cancer Therapy", in Monoclonal Antibodies for Cancer Detection and Therapy, Baldwin et al. (eds), pp. 303-16 (Academic Press 1985)).

In one example, the linker-chelator tiuexutan is conjugated to a compound that binds CTR, by a stable thiourea covalent bond to provide a high-affinity chelation site for Indium-111 or Yttrium-90.

The skilled person will appreciate that there are a number of bacterial or plant polypeptide toxins that are suitable for use as cytotoxic agents in the methods of the invention. These polypeptides include, but are not limited to, polypeptides such as native or modified *Pseudomonas* exotoxin (PE), diphtheria toxin (DT), ricin, abrin, gelonin, momordin II, bacterial RIPs such as shiga and shiga-like toxin a-chains, luffin, atrichosanthin, momordin I, Mirabilis anti-viral protein, pokeweed antiviral protein, byodin 2 (U.S. Pat. No. 5,597,569), gaporin, as well as genetically engineered variants thereof. Native PE and DT are highly toxic compounds that typically bring about death through liver toxicity. Preferably, PE and DT are modified into a form that removes the native targeting component of the toxin, e.g., domain Ia of PE and the B chain of DT. One of skill in the art will appreciate that the invention is not limited to a particular cytotoxic agent.

In some embodiments, the cytotoxic agent may be a polypeptide fused to a compound that binds CTR. Fusion polypeptides comprising a compound that binds CTR may be prepared by methods known to one of skill in the art. For example, a gene encoding an Fv region is fused to a gene encoding a cytotoxic agent. Optionally, the Fv gene is linked to a segment encoding a peptide connector. The peptide connector may be present simply to provide space between the compound that binds CTR and the cytotoxic agent or to facilitate mobility between these regions to enable them to each attain their optimum conformation. The DNA sequence comprising the connector may also provide sequences (such as primer sites or restriction sites) to facilitate cloning or may preserve the reading frame between the sequence encoding the binding moiety and the sequence encoding the cytotoxic agent. The design of such connector peptides is well known to those of skill in the art.

Generally producing fusion polypeptides involves, e.g., separately preparing the Fv light and heavy chains and DNA encoding any other protein to which they are fused and recombining the DNA sequences in a plasmid or other vector to form a construct encoding the particular desired fusion polypeptide. However, a simpler approach involves inserting the DNA encoding the particular Fv region into a construct already encoding the desired second polypeptide. The DNA sequence encoding the Fv region is inserted into the construct using techniques well known to those of skill in the art.

Compounds that bind CTR, e.g., recombinant single chain antibodies, may be fused to, or otherwise bound to the cytotoxic agent by any method known and available to those in the art. The two components may be chemically bonded together by any of a variety of well-known chemical procedures. For example, the linkage may be by way of heterobifunctional cross-linkers, e.g., SPDP, carbodiimide, glutaraldehyde, or the like. Production of various immunotoxins, as well as chemical conjugation methods, are well-known within the art (see, for example, "Monoclonal Antibody-Toxin Conjugates: Aiming the Magic Bullet," Thorpe et al., Monoclonal Antibodies in Clinical Medicine, Academic Press, pp. 168-190 (1982); Waldmann, 1991; Vitetta et al., 1987; Pastan et al., 1986; and Thorpe et al., 1987).

It will be appreciated that methods of treating leukemia involving the use of compounds that bind CTR may be performed in isolation or as an adjunct to known leukemia therapy regimes. For example, treatment may be conducted in conjunction with or after treatments such as chemotherapy, radiation therapy, stem cell transplant and/or immunotherapy, for example, monoclonal antibody therapy. Examples of chemotherapeutic agents used in the treatment of leukemia include chlorambucil, cyclophosphamide, melphalan, daunorubicin, doxorubicin, idarubicin, mitoxantrone, methotrexate, fludarabine, cytarabine, etoposide, topotecan, prednisone, dexamethasone, vincristine and vinblastine.

Production of Genetically Modified Cells

In one embodiment, the present invention relates to the use of genetically modified cells, particularly genetically modified CTR+/CD34+ cells. Preferably, the cells are genetically modified to produce a cytotoxic agent or biological response modifier. Typically, the cells will be genetically modified such that the heterologous protein is secreted from the cells. However, in an embodiment the cells can be modified to express a functional non-protein encoding polynucleotide such as dsRNA (typically for RNA silencing), an antisense oligonucleotide or a catalytic nucleic acid (such as a ribozyme or DNAzyme).

Genetically modified cells may be cultured in the presence of at least one cytokine in an amount sufficient to support growth of the modified cells. The genetically modified cells thus obtained may be used immediately (e.g., in transplant), cultured and expanded in vitro, or stored for later uses. The modified cells may be stored by methods well known in the art, e.g., frozen in liquid nitrogen.

Genetic modification as used herein encompasses any genetic modification method which involves introduction of an exogenous or foreign polynucleotide into an adult multipotential cell or modification of an endogenous gene within adult multipotential cell. Genetic modification includes but is not limited to transduction (viral mediated transfer of host DNA from a host or donor to a recipient, either in vitro or in vivo), transfection (transformation of cells with isolated viral DNA genomes), liposome mediated transfer, electroporation, calcium phosphate transfection or coprecipitation and others. Methods of transduction include direct co-culture of cells with producer cells (Bregni et al., 1992) or culturing with viral supernatant alone with or without appropriate growth factors and polycations (Xu et al., 1994).

An exogenous polynucleotide or transgene is preferably introduced to a host cell in a vector. The vector preferably includes the necessary elements for the transcription and translation of the inserted coding sequence. Methods used to construct such vectors are well known in the art. For example, techniques for constructing suitable expression vectors are described in detail in Sambrook et al., Molecular Cloning: A Laboratory Manual, Cold Spring Harbor Press, N.Y. (3rd Ed., 2000); and Ausubel et al., Current Protocols in Molecular Biology, John Wiley & Sons, Inc., New York (1999).

Vectors may include but are not limited to viral vectors, such as retroviruses, adenoviruses, adeno-associated viruses, and herpes simplex viruses; cosmids; plasmid vectors; synthetic vectors; transposons and other recombination vehicles typically used in the art. Vectors containing both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). Specific examples include, pSG, pSV2CAT, pXt1 from Stratagene; and pMSG, pSVL, pBPV and pSVK3 from Pharmacia.

Preferred vectors include retroviral vectors (see, Coffin et al., "Retroviruses", Chapter 9 pp; 437-473, Cold Springs Harbor Laboratory Press, 1997). Vectors useful in the invention can be produced recombinantly by procedures well known in the art. For example, WO94/29438, WO97/21824 and WO97/21825 describe the construction of retroviral packaging plasmids and packing cell lines. Exemplary vectors include the pCMV mammalian expression vectors, such as pCMV6b and pCMV6c (Chiron Corp.), pSFFV-Neo, and pBluescript-Sk+. Non-limiting examples of useful retroviral vectors are those derived from murine, avian or primate retroviruses. Common retroviral vectors include those based on the Moloney murine leukemia virus (MoMLV-vector). Other MoMLV derived vectors include, Lmily, LINGFER, MINGFR and MINT. Additional vectors include those based on Gibbon ape leukemia virus (GALV) and Moloney murine sarcoma virus (MOMSV) and spleen focus forming virus (SFFV). Vectors derived from the murine stem cell virus (MESV) include MESV-MiLy. Retroviral vectors also include vectors based on lentiviruses, and non-limiting examples include vectors based on human immunodeficiency virus (HIV-1 and HIV-2).

In producing retroviral vector constructs, the viral gag, pol and env sequences can be removed from the virus, creating room for insertion of foreign DNA sequences. Genes encoded by foreign DNA are usually expressed under the control a strong viral promoter in the long terminal repeat (LTR). Selection of appropriate control regulatory sequences is dependent on the host cell used and selection is within the skill of one in the art. Numerous promoters are known in addition to the promoter of the LTR. Non-limiting examples include the phage lambda PL promoter, the human cytomegalovirus (CMV) immediate early promoter; the U3 region promoter of the Moloney Murine Sarcoma Virus (MMSV), Rous Sacroma Virus (RSV), or Spleen Focus Forming Virus (SFFV); Granzyme A promoter; and the Granzyme B promoter. Additionally inducible or multiple control elements may be used. The selection of a suitable promoter will be apparent to those skilled in the art.

Such a construct can be packed into viral particles efficiently if the gag, pol and env functions are provided in trans by a packing cell line. Therefore, when the vector construct is introduced into the packaging cell, the gag-pol and env proteins produced by the cell, assemble with the vector RNA to produce infectious virons that are secreted into the culture medium. The virus thus produced can infect and integrate into the DNA of the target cell, but does not produce infectious viral particles since it is lacking essential packaging sequences. Most of the packing cell lines currently in use have been transfected with separate plasmids, each containing one of the necessary coding sequences, so that multiple recombination events are necessary before a replication competent virus can be produced. Alternatively the packaging cell line harbours a provirus. The provirus has been crippled so that although it may produce all the proteins required to assemble infectious viruses, its own RNA cannot be packaged into virus. RNA produced from the recombinant virus is packaged instead. Therefore, the virus stock released from the packaging cells contains only recombinant virus. Non-limiting examples of retroviral packaging lines include PA12, PA317, PE501, PG13, PSI.CRIP, RDI 14, GP7C-tTA-G10, ProPak-A (PPA-6), and PT67. Reference is made to Miller et al., 1986; Miller et al., 1989; Danos et al., 1988; Pear et al., 1993; and Finer et al., 1994.

Other suitable vectors include adenoviral vectors (see, Frey et al., 1998; and WO 95/27071) and adeno-associated viral vectors. These vectors are all well known in the art, e.g., as described in Chatterjee et al., 1996; and Stem Cell Biology and Gene Therapy, eds. Quesenberry et al., John Wiley & Sons, 1998; and U.S. Pat. Nos. 5,693,531 and 5,691,176. The use of adenovirus-derived vectors may be advantageous under certain situation because they are not capable of infecting non-dividing cells. Unlike retroviral DNA, the adenoviral DNA is not integrated into the genome of the target cell. Further, the capacity to carry foreign DNA is much larger in adenoviral vectors than retroviral vectors. The adeno-associated viral vectors are another useful delivery system. The DNA of this virus may be integrated into non-dividing cells, and a number of polynucleotides have been successful introduced into different cell types using adeno-associated viral vectors.

In some embodiments, the construct or vector will include two or more heterologous polynucleotide sequences. Preferably the additional nucleic acid sequence is a polynucleotide which encodes a selective marker, a structural gene, a therapeutic gene, or a cytokine/chemokine gene.

A selective marker may be included in the construct or vector for the purposes of monitoring successful genetic modification and for selection of cells into which DNA has been integrated. Non-limiting examples include drug resistance markers, such as G148 or hygromycin. Additionally negative selection may be used, for example wherein the marker is the HSV-tk gene. This gene will make the cells sensitive to agents such as acyclovir and gancyclovir. The NeoR (neomycin/G148 resistance) gene is commonly used but any convenient marker gene may be used whose gene sequences are not already present in the target cell can be used. Further non-limiting examples include low-affinity Nerve Growth Factor (NGFR), enhanced fluorescent green protein (EFGP), dihydrofolate reductase gene (DHFR) the bacterial hisD gene, murine CD24 (HSA), murine CD8a(lyt), bacterial genes which confer resistance to puromycin or phleomycin, and β-glactosidase.

The additional polynucleotide sequence(s) may be introduced into the host cell on the same vector or may be introduced into the host cells on a second vector. In a preferred embodiment, a selective marker will be included on the same vector as the polynucleotide.

The present invention also encompasses genetically modifying the promoter region of an endogenous gene such that expression of the endogenous gene is up-regulated resulting in the increased production of the encoded protein compared to a wild type cells.

Pharmaceutical Compositions, Dosages, and Routes of Administration

Compositions comprising a compound that binds CTR together with an acceptable carrier or diluent are useful in the methods of the present invention.

Therapeutic compositions can be prepared by mixing the desired compounds having the appropriate degree of purity with optional pharmaceutically acceptable carriers, excipients, or stabilizers (Remington's Pharmaceutical Sciences, 16th edition, Osol, A. ed. (1980)), in the form of lyophilized formulations, aqueous solutions or aqueous suspensions. Acceptable carriers, excipients, or stabilizers are preferably nontoxic to recipients at the dosages and concentrations employed, and include buffers such as Tris, HEPES, PIPES, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; sugars such as sucrose, mannitol, trehalose or sorbitol; salt-forming counter-ions such as sodium; and/or non-ionic surfactants such as TWEEN™, PLURONICS™ or polyethylene glycol (PEG).

Additional examples of such carriers include ion exchangers, alumina, aluminum stearate, lecithin, serum proteins, such as human serum albumin, buffer substances such as glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, colloidal silica, magnesium trisilicate, polyvinyl pyrrolidone, and cellulose-based substances.

Therapeutic compositions to be used for in vivo administration should be sterile. This is readily accomplished by filtration through sterile filtration membranes, prior to or following lyophilization and reconstitution. The composition may be stored in lyophilized form or in solution if administered systemically. If in lyophilized form, it is typically formulated in combination with other ingredients for reconstitution with an appropriate diluent at the time for use. An example of a liquid formulation is a sterile, clear, colorless unpreserved solution filled in a single-dose vial for subcutaneous injection.

Therapeutic compositions generally are placed into a container having a sterile access port, for example, an intravenous solution bag or vial having a stopper pierceable by a hypodermic injection needle. The compositions are preferably administered parenterally, for example, as intravenous injections or infusions or administered into a body cavity.

The growth of CTR expressing cells may be inhibited or reduced by administering to a subject in need of the treatment an effective amount of a composition comprising a compound that binds CTR. The compound may be administered in an amount of about 0.001 to 2000 mg/kg body weight per dose, and more preferably about 0.01 to 500 mg/kg body weight per dose. Repeated doses may be administered as prescribed by the treating physician.

Single or multiple administrations of the compositions are administered depending on the dosage and frequency as required and tolerated by the patient. The dosage and frequency will typically vary according to factors specific for each patient depending on the specific therapeutic or prophylactic agents administered, the severity and type of leukemia or cardiovascular disease, the route of administration, as well as age, body weight, response, and the past medical history of the patient. Suitable regimens can be selected by one skilled in the art by considering such factors and by following, for example, dosages reported in the literature and recommended in the Physician's Desk Reference (56$^{th}$ ed., 2002). Generally, the dose is sufficient to treat or ameliorate symptoms or signs of disease without producing unacceptable toxicity to the patient.

In one example of the present invention, a radiolabeled form of the compound that binds CTR is delivered by intravenous injection as a therapeutic agent to target cells that express CTR. Previous examples of radiolabeled antibodies and the methods for their administration to patients as therapeutics are known to those skilled in the art. Examples include Iodine$^{131}$ labeled Lym-1, against the β subunit of HLA-DR (DeNardo et al., 1988; DeNardo et al. 1987) and the anti-CD20 Indium$^{111}$ and Yttrium$^{90}$ labeled Ibritumomab Tiuxetan (IDEC-Y2B8, ZEVALIN®) and Iodine I 131 Tositumomab (BEXXAR®).

In any treatment regimen, the therapeutic composition may be administered to a patient either singly or in a cocktail containing other therapeutic agents, compositions, or the like, including, but not limited to, immunosuppressive agents, tolerance-inducing agents, potentiators and side-effect relieving agents. Examples of immunosuppressive agents include prednisone, melphalain, prednisolone, DECADRON (Merck, Sharp & Dohme, West Point, Pa.), cyclophosphamide, cyclosporine, 6-mercaptopurine, methotrexate, azathioprine and i.v. gamma globulin or their combination. Preferred potentiators include monensin, ammonium chloride, perhexyline, verapamil, amantadine and chloroquine. All of these agents are administered in generally accepted efficacious dose ranges such as those disclosed in the Physician's Desk Reference, 41st Ed., Publisher Edward R. Barnhart, N.J. (1987).

EXAMPLES

Example 1

Production of Antibodies

These studies involved the use of several anti-CTR antibodies: a rabbit, anti-rodent CTR polyclonal (PAb 189/10 Welcome Receptor. Antibodies Pty Ltd, Melbourne; also catalogued as AHP 635, AbD Serotec, UK); an anti-human/rabbit CTR monoclonal (MAb 31-01, WRA, Melbourne; also known as MCA 2191, AbD Serotec, UK); an anti-human/rabbit CTR mouse monoclonal antibody (MAb 1C11; WRA) and an anti-human/rabbit CTR mouse monoclonal antibody (MAb 9B4; WRA). The former polyclonal antibody was raised in rabbits against a conjugated peptide equivalent to a sequence located within the carboxyl domain of rat CTR that is predicted to lie within the cytoplasm (epitope 1; SEQ ID NO: 8), and has been described in more detail previously (Tikellis et al., 2003; Tolcos et al., 2003). The mouse monoclonal (MAb 31-01 or MCA 2191, IgG 2A) was raised against a similar epitope of human/rabbit CTR DIPIY-ICHQEPRNEPANN (human; SEQ ID NO: 3) and GIPVY-IYHQEPRNDPAHS (rabbit; SEQ ID NO: 4) using standard techniques for monoclonal production as described (Tikellis et al., 2003). The mouse monoclonal antibodies MAb 1C11 (IgM) and MAb 9B4 (IgG2A) are directed against an epitope within the extracellular domain (epitope 4) of human/rabbit CTR PSEKVTKYCDEKGVWFK (human; SEQ ID NO: 5) and PTEKVTKYCDETGVWFK (rabbit; SEQ ID NO: 6). These antibodies were also verified using ELISA assays, and FACS, IHC and RT-PCR analyses of the CTR-positive cell line K-562.

Preparation of Polyclonal Antibodies Raised against Calcitonin Receptor

The immunogen was prepared by a modification of the method of Butler et al. (1990). Synthetic peptide (5 mg, Chiron, Melbourne, Australia) and 25 mg porcine thyroglobulin (Sigma, St. Louis, Mo.) were reacted with 5 mg ethyl-carbodiimide in 4 mL of 10 mM phosphate buffered saline pH 7.5 at 4° C. for 24 hours. Trace amounts of [$^{125}$I]-peptides added into the reaction, revealed less than 5% conjugation by Sephadex G75 gel filtration. Addition of 40 µL of 25% aqueous glutaraldehyde and a further 72 hours at 4° C. resulted in over 80% conjugation. Gel filtration was used to purify the rest of the conjugated material over four column runs, pooled and stored frozen, in aliquots for ten immunizations. The first immunogen was emulsified with equal volumes of Freund's Complete Adjuvant. Subsequent immunizations used incomplete adjuvant. The antiserum was partially purified by chromatography using 1 mL columns packed with Protein A-sepharose (Pharmacia, Sweden) and low pressure chromatography, eluted at low pH (Ey et al., 1978), neutralized, dialyzed and finally lyophilized under vacuum.

In an ELISA plate test the peptide used to raise this antibody against CTR, was absorbed onto the surface of 96-well plastic plates at a concentration of 2 µg/mL in carbonate buffer, pH 9. The dilution of the antibody that resulted in 50% colour development was approximately 1:100,000.

Preparation of Antibodies by Monoclonal Fusion

Mice (2×BALB/c and 2×C57Bl/6) were immunized with approximately 25 ug/mouse antigen (conjugated peptides equivalent to epitopes 4 and 5 of CTR) in Complete Freund's Adjuvant intra-peritoneally (i/p), then boosted 4 weeks later with approximately 10 µg/mouse i/p in Incomplete Freund's Adjuvant (IFA). Mice were bled and serum titres assayed by ELISA. Generally after a second or third boost (antigen in PBS), titres were high enough (>1:1000) to proceed to fusion.

The mouse with the highest reactivity was selected and was boosted with 10 µg antigen total in PBS, half i/p and half i/v, 4 days prior to fusion.

On the day of fusion, the spleen was removed, a single cell suspension prepared, and the cells were washed twice in DME. SP2/O cells were washed twice in DME to remove all FCS, and adjusted to 5×10$^7$-10$^8$ cells per fusion with 1 mouse spleen. Spleen cells and SP2/Os were pelleted together, then the fusion performed by addition of 1 ml warm PEG 1500 to the pellet with stirring for 1 minute. The fusion mixture was then slowly diluted to 25 ml with DME. Cells were centrifuged and resuspended in Hybridoma Serum Free Medium containing 10% FCS, IL-6 conditioned medium and HAT, and plated out to 5-6 microtiter plates.

Plates were fed (½ medium removed and replaced with fresh) at Days 3, 6 and 8-9. When cells were confluent, (usually Day 10-14) supernatants were removed and assayed (usually by ELISA) to identify positive wells. Cells from positive wells were expanded to 6 mL cultures, then 2-3 freezings of each were made and cells stored in liquid nitrogen.

Supernatants from cultures were then tested by immunohistochemistry, ELISA test and positive cells selected for limit dilution cloning. Usually 2 rounds of cloning were necessary to ensure the hybridomas were clonal.

rows of eight AML patients were tested for expression of CTR using the anti-human CTR monoclonal antibody MCA 2191 (AbD Serotec, UK). CTR expression in precursor cells of 5 of the 8 positive AML patients is shown in FIG. 1.

The CTR-positive cells are localised suggesting proliferation from a precursor or alternatively recruitment to a loci that has high concentrations of a growth factor. The appearance of the cells with a large nucleus and distinctive chromatin pattern is typical of a subpopulation of blast cells.

Example 3

Flow Analysis of Calcitonin Receptor (MAb 1C11, Epitope 4) and CD34 Expression in Normal, AML and ALL Samples A frozen stock of mononuclear cells (MNCs) was thawed and washed with 1×PBS/2% fetal bovine serum (FBS). 0.5-1×10$^6$ cells were resuspended in 100 µl 1×PBS/2% FBS for each reaction. Antibodies were added according to Table 1:

TABLE 1

Antibodies used for FACS analysis.

| Isotype control | CD34 staining | CTR staining | CD34 + CTR co-staining |
|---|---|---|---|
| 2 µl ISO-Mouse IgM (BD Pharmingen, Cat # 553472) | 5 µl CD34-PE (Becton Dickinson, Cat # 348057) | 4 µl MAb 1C11 | 5 µl CD34-PE (Becton Dickinson, Cat # 348057) |
| 5 µl ISO-Mouse IgG-PE (Becton Dickinson Cat # 349043) | 2 µl ISO-Mouse IgM (BD Pharmingen, Cat # 553472) | 5 µl ISO-Mouse IgG-PE (Becton Dickonson Cat # 349043) | 4 µl MAb 1C11 |

The isotype of MAbs was determined and MAb containing supernatants were collected.

Example 2

Immunohistochemical Staining for CTR in Bone Marrows of AML Patients

Immunohistochemical staining of bone marrows was performed as follows:

Paraffin sections were prepared from 4% paraformaldehyde fixed, paraffin-embedded human bone marrow.

Sections were de-waxed and hydrated.

Epitopes were unmasked using Decloaking Chamber (Biocare Medical, Walnut Creek, Calif., USA) with Universal Decloaker Solution according to manufacturer's protocol.

Sections were permeabilized with PBS/0.2% triton X100 for 20 min at room temperature.

Endogenous peroxidase was quenched by incubating the sections for 5 minutes in 0.3% (vol/vol) hydrogen peroxide in PBS.

Non-specific binding sites were blocked by incubation for 20 minutes with 5% BSA/PBS.

The sections were incubated with primary antibodies (monoclonal anti-calcitonin receptor MCA 2191; 1:200) at room temperature overnight.

After washing in PBS, specific staining was detected using the MACH 3, mouse-probe HRP polymer kit (Biocare).

After thorough washing, the detection step was carried out using 3,3'-diaminobenzidine as the chromogen.

Sections were lightly counter-stained with hematoxylin.

In this study, immunohistochemistry and anti-calcitonin receptor (CTR) antibodies were used to determine expression of CTR in bone marrow from AML patients. The bone mar- Following incubation on ice for 30 min, the cells were rinsed with 1×PBS/2% FBS and resuspended in 100 µl 1×PBS/2% FBS. 2 µl goat α-mouse IgM-FITC (Zymed, catalogue #62-6811) was added to each reaction.

The cells were incubated on ice for an additional 30 min and rinsed with 1×PBS/2% FBS and resuspended in approximately 200 µl-300 µl 1×PBS/2% FBS for each reaction.

Prior to loading the samples on the FACS machine, 2 µg of propidium iodide (PI) was added to each reaction.

Propidium iodide positive cells were gated out. The thresholds of both CD34-PE+ and CTR-FITC+ were set at first log. Cells with fluorescent intensity above first log in comparison to isotype controls were considered to be positive. The results are summarised in Table 2.

Example 4

Detection of CTR Expression with MAb 9B4

CTR expression was detected in K562 cells using the CSA II System (Dako, Code K1497) as follows:

Specimens were covered with Hydrogen Peroxide and incubated for 5 min prior to washing with distilled water. Excess liquid was removed and enough Protein Block was added to cover the specimen and incubated for 5 minutes.

Excess Protein Block was removed. 1 mg/ml MAb 9B4 was diluted 1:500 in DAKO diluent and incubated with the specimen at 4° C. overnight. Slides were rinsed in wash buffer and placed in up to three TBST buffer baths for 3-5 minutes each.

Slides were wiped to remove excess buffer, enough Anti-Mouse Immunoglobulins-HRP was added to cover the specimen and incubated for 15 minutes.

TABLE 2

Summary of human leukemia and normal bone marrow samples analysed by FACS to determine the sizes of the CTR+ blast cell (CD34+) populations.

| Type of Leukaemia | Sub-Category | Number of Samples | % CTR+/CD34+* | | % Disease Category | |
|---|---|---|---|---|---|---|
| | | | 0.5%-2.5% | >2.5%-15% | 0.5%-2.5% | >2.5% |
| ALL | Not Available | 12 | 4 | 5 | 33% | 42% |
| AML | — | 8 | 1 | 1 | | |
| | MLD | 2 | 1 | 1 | | |
| | M1 | 1 | 1 | | 31% | 12.5% |
| | M2 | 2 | 1 | 0 | | |
| | M5 | 3 | 1 | 0 | | |
| | | TOT = 16 | | | | |
| Normal Bone Marrow | | 6 | 2 | 0 | 33% | 0% |
| Cell Lines | | | | | | |
| Nalm 20 | B cell precursor | | 1 | — | | |
| Jurkat | ALL | | — | 1 | | |
| NB4 | AML FAB M3 | | 1 | — | | |
| HPB-ALL | ALL | | — | — | | |

In summary, greater than 40% of patients (n=12) diagnosed with ALL have large populations (2.7-10.6%) of CTR+/CD34+ cells in their bone marrow, compared to 13% amongst the AMLs (n=16) and 0% in the normals (n=6).

The slides were rinsed in wash buffer as described above and placed in up to three fresh wash buffer baths for 3-5 min each.

Slides were protected from light and incubated for 15 min with enough Amplification Reagent to cover the specimen. The slides were rinsed as before and placed in up to three fresh wash buffer baths of 3-5 min each.

Slides were wiped around the specimen to remove excess buffer. The slides were then incubated for 15 min with enough Anti-Fluoroscein-HRP to cover the specimen. The slides were rinsed as before and placed in up to three fresh wash buffer baths of 3-5 min each. The slides were wiped and Liquid DAB Substrate Chromagen was added to cover the specimen and incubated for 5 min prior to rinsing with distilled water.

FIG. 2 shows K562 cells that were incubated in the presence or absence of sodium butyrate and stained with MAb 9B4.

Example 5

Mouse Model of Wound Healing

Mice (C57/B6, male, aged 8 weeks) were anaesthetised by inhalation using a mixture of ethrane/air. The skin in the mid dorsal region of the back was shaved, washed with antiseptic and a full thickness skin wound measuring 1 cm×1 cm was made using a scalpel. The wound was then irrigated with sterile saline and allowed to heal. Wound tissue was harvested at various time points after wounding and fixed in 4% paraformaldehyde/PBS (Darby et al., 1997).

While little expression of CTR was evident in the control skin (FIG. 3A), CTR was demonstrated in endothelial cells of nascent blood vessels and other morphologically distinct cell types within the granulation tissue undergoing healing at 7 days (panels C, B & D), 10 days (panels E & F) and 12 days (panels G & H). There were also other smaller, rounder cells that stain positively for CTR (panels B & D). The numbers of CTR-positive cell types reached a maximum around seven days during the healing process although the presence of the smaller rounder cells persisted to ten and twelve days (panels F & H).

Example 6

Rabbit Model of Atherosclerosis

Rabbits (male, New Zealand whites) were fed a standard chow (controls) diet and supplemented with 0.5% cholesterol for 4 weeks or 1% methionine/0.5% cholesterol for 12 weeks. The rabbits were anaesthetised (ketamine [10 mg/kg] and xylazine [3 mg/kg], intravenous) prior to surgery, a segment of the abdominal arteries or thoracic aortas were removed and prepared for IHC beginning with fixation in 4% paraformaldehyde/phosphate buffered saline (PBS, pH 7.2) as described by Zulli et al., (2003 and 2006).

The development of atherosclerotic plaque is an early feature of vascular disease in rabbits fed a diet supplemented with 0.5% cholesterol for only four weeks (FIG. 4). The association of CTR expression with diseased segments of abdominal arteries is further emphasized in FIG. 4A (MAb 31-01) in which cells of the endothelial layer adjacent to plaque were CTR-negative, while those within or close to plaque were CTR-positive. In FIG. 4, B (MAb 31-01) & C (MAb 1C11), a similar staining pattern was found with monoclonal antibodies raised to two separate epitopes of CTR. These images were further magnified in FIGS. 4 (D & E) in which flattened CTR-positive cells were evident in the endothelial layer. In this new plaque lipid-laden foam cells were also common. A majority of these CTR-positive cells were also positive for the precursor cell marker CD34 (FIG. 4F).

In rabbits fed a diet of 1% methionine and 0.5% cholesterol for 12 weeks, cardiovascular disease was investigated in the coronary arteries (data not shown) and the thoracic aortas (FIG. 5). In these latter vessels intimal thickening (panels C & D) together with atherosclerotic plaque (panels E & F) can readily be demonstrated compared to a control (panels A & B). In controls the detectible levels of CTR expression were either low or negative within the endothelial layer. However, as an example and shown in FIG. 5B, CTR-positive blood-borne cells were found within the vessel lumen. Within diseased vessels CTR-positive cells were found integrated into the endothelial layer (panels C-F) as well as being found deep within the plaque itself (FIG. 5F).

Table 3 summarizes the of quantification (relative intensity X proportional area) of the CTR-positive endothelial cells that overlie normal intima, thickened neo-intima and atherosclerotic plaque in control animals and those in which cardiovascular disease (CVD) had been induced with a supplemented diet of 1% methionine/0.5% cholesterol for twelve weeks. There is a significant difference (p=0.008, two-tailed t-test) between expression of CTR by endothelial cells in controls versus diseased tissues (see images in FIG. 5).

TABLE 3

Comparison of CTR-positive regions (relative intensity × proportional area (Zulli et al., 2006)) of endothelial layers associated with normal intima, expanded intima and overlying atherosclerotic plaque in thoracic aortas control rabbits (n = 5) and those with CVD, fed 1% methionine/0.5% cholesterol (n = 5) for 12 weeks (see FIG. 5). Significance was established using the two-tailed t-test (*), p < 0.008.

| Source of Thoracic Artery | CTR-positive endothelium overlying: | | |
|---|---|---|---|
| | Normal imtima | Expanded neo-intima | Atherosclerotic plaque |
| Control animals | 1.0 ± 0.49 | 0.7 ± 0.40* | N/A |
| CVD animals | 1.86 ± 0.56 | 2.90 ± 0.42* | 3.22 ± 0.21 |

Example 7

Calcitonin Receptor Expression in Human Diseased Blood Vessels

Human Blood Vessels and Preparation

Segments of human blood vessels were obtained as remnants from patients undergoing coronary artery bypass grafting (CABG). These included internal mammary arteries (IMA) and radial arteries (RA). Patients aged 48 to 70 years gave informed consent and were receiving a variety of medications, including HMG CoA reductase inhibitors, ACE inhibitors, nitrates and beta adreno-receptor blockers. Harvesting was performed using techniques previously established in surgery (Zulli et al., 2006). In particular, all vessels were treated with papaverine in situ prior to CABG. Only non-traumatised vessel segments were used in this study.

After CABG was completed, remnants of radial arteries were placed directly into containers containing oxygenated (5% $CO_2$, 95% $O_2$) Krebs-Henseleit solution [(mM): NaCl 118, KCl 4.7, NaHCO3 1.2, MgSO4 2.5, Glucose 5.5] and transported to the laboratory on ice. Upon arrival, arterial segments were placed on a Petri dish on ice and prepared for further processing by removal of adjoining adipose. Prior to immunohistochemical staining the segments of arteries were fixed in 4% para-formaldehyde/PBS (16 hours, room-temperature) and were then processed and embedded in paraffin blocks. Sections were cut 5 µm thick and mounted on glass slides.

Immunohistochemistry

In the IHC protocol followed for images as shown in FIG. 6, the monoclonal anti-human CTR antibody MAb 31-01 was achieved with dilution of 1:500 (FIG. 6, A-G) and the slides incubated overnight with primary antibody. Staining with the polyclonal antibody PAb 189/10 (Tikellis et al., 2003; Tolcos et al., 2003) was diluted 1:200 (FIG. 6H). Normal rabbit serum was used as the negative control.

Immunohistochemistry was performed as described (Zulli et al., 2006), following the protocol supplied by the manufacturer (Envision Plus HRP [horseradish peroxidase], DAKO Corporation, Carpinteria, Calif., USA). Colour was developed using DAB (diaminobenzidine) except in FIG. 6H when the dye used was AEC (3-amino-9-ethylcarbazole), resulting in a red/pink colour. The counterstain was haematoxylin (Amber Scientific, Australia).

In FIG. 6 are shown representative images of immunohistochemical staining using the mouse monoclonal anti-human CTR antibody MAb 31-01 (panels A-G) and polyclonal PAb 189/10 (panel H). In the low power images (FIG. 6, panels A & H) it is evident that CTR is expressed by similar cells and structures within the diseased human radial artery, detected using either antibody. These images represent a standard outcome of staining for CTR that is associated with human vascular disease. Cells that express CTR within the organizing thrombis (FIG. 6A) were more clearly identified at higher magnification as shown in FIG. 6, panels B-D. These include endothelial cells of the re-canulated, organized thrombis (examples indicated by arrows) surrounded by positive cells with small densely stained nuclei (examples indicated with arrowheads in panels B-D).

Within the media (FIGS. 6, A & H) there are many repetitive elongated structures that stain positively for CTR and are aligned with the smooth muscle cells in most instances.

Within the vasa vasorum of this diseased radial artery, vessels were also found with CTR-positive cells incorporated into the vessel wall (panels E & F), fibroblast-like cells (arrow heads) and smaller round cells in the surrounding parenchyma. Of note is the CTR-positive nucleated cell within the lumen of the blood vessel (venule, FIG. 6F).

Within a human diseased internal mammary artery some CTR-positive cells were found apparently adherent to the endothelial layer while others were further incorporated (arrowed). CTR-positive fibroblast-like cells were also found in the neo-intima of these vessels (FIG. 6G, arrowheads).

The polyclonal antibody PAb 189/10 does cross-react with human CTR and this property was used to check the coincidence of staining using these two antibodies. It is clear that a very similar staining pattern was achieved whether using the polyclonal PAb 189/10 (FIG. 6H) or monoclonal MAb 31-01 antibodies (FIG. 6A).

In FIG. 7 semi-quantification was performed as previously described (Zulli et al., 2006). The product of the Intensity and Proportional Area of staining (Intensity X Proportional Area) was generated using a computer coupled to a digital camera and integrated for image analysis. The statistical significance for the correlation was calculated by the method of Pearson on GraphPad. The statistical significance, radial arteries versus internal mammary arteries, was established using the Students' two tailed t-test.

In FIG. 7 is shown correlations of data from the quantification (relative intensity X proportional area, IxPA) of the CTR-positive endothelium, intima and media within the internal mammary arteries (IMA, FIG. 7A) and radial arteries (RA, FIG. 7B). In our samples, IMAs had examples of both non-diseased segments (normal intima, FIG. 7A) and diseased segments (FIG. 6G) with thickened neo-intima, in contrast to the samples of RAs, in which only diseased regions were found (FIG. 7B). The IxPA was determined for regions that varied in the ratio of neo-intima/media.

There was a significant difference (Students' t-test) in the IxPA for CTR expression measured in the endothelium, intima and media from RAs versus IMAs (see FIG. 7C).

When the data was combined for RAs and IMAs there was also a significant correlation (Pearson algorithm from GraphPad) between the IxPA and the intimal/media ratio for each of the endothelium, neo-intima and media (FIG. 7C).

The novel observation of the expression of CTR in blood vessels and by specific cells in the surrounding parenchyma in two different physiological (healing wound) and pathophysiological contexts, namely those of atherosclerotic plaque and more advanced cardiovascular disease, are described here.

In the granulation tissues of healing mouse wounds CTR was expressed by endothelial cells of nascent blood vessels, fibroblast-like cells and a further population of smaller cells reaching maximum expression about 7 days during the healing process (FIG. 3). As the tissue returned to an ordered (healed) state CTR expression was decreased (indicating transitory expression) in positive cells throughout the region of healing.

The present inventors also studied more advanced cardiovascular disease in rabbits induced with a diet supplemented with both 1% methionine and 0.5% cholesterol for 12 weeks (FIG. 5). It has previously been found that the arteries from these animals have a dysfunctional endothelium in terms of relaxation responses to vasodilators when tested in organ bath experiments (Zulli et al., 2003). In this advanced rabbit model of cardiovascular disease, the neo-intima has been enlarged and there were many examples of atherosclerotic plaque, although there are no apparent pathologies associated with the media. In this model, cells that are CTR-positive include endothelial cells that overlay an expanded neo-intima and plaque, and foam cells and fibroblast-like (SMA-positive) cells within atherosclerotic plaques themselves. Immunoquantification data that uses the product of intensity of staining and proportional area (Table 3) provides statistical confirmation of the staining in the endothelium as illustrated in FIG. 5.

It has been established that cells may be recruited from peripheral blood (which, in turn, may originate from populations in the bone marrow and other organs) into regions of cardiovascular disease. The data shown in FIG. 4 is consistent with a model of CTR-positive precursor cells migrating from the blood stream into the neo-intima and plaque. In rabbits fed a diet supplemented with 0.5% cholesterol for only 4 weeks, many of the endothelial cells and other adherent cells that are associated with atherosclerotic plaques (FIG. 4), are CTR-positive in contrast to the endothelium a short distance away, which is CTR-negative. Together these data are consistent with a model in which CTR-positive cells present in cardiovascular originate from bone marrow as CD 34-positive precursors and represent a subpopulation of multipotent adult progenitor cells.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

All publications discussed above are incorporated herein in their entirety.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Beychok (1979) Cells of Immunoglobulin Synthesis, Academic Press, New York, p 69.
Bird et al. (1988) Science. 242:423-426.
Bregni et al. (1992) Blood. 80:1418-1422.
Butler et al. (1990) Diabetes. 39:752-756.
Campbell et al. (2001) Ann N Y Acad. Sci. 947:18-24.
Chatterjee et al. (1996) Curr Top Microbiol Immunol. 218: 61-73.
Colcher et al. (1986) Methods Enzymol. 121: 802-816.
Copp et al. (1962) Endocrinology. 70:638-649.
Dacquin et al. (2004) J Cell Biol. 164:509-514.
Danos et al. (1988) Proc Natl Acad Sci USA. 85:6460-6464.
Darby et al. (1997) Int J Biochem Cell Biol. 29:191-200.
DeNardo et al. (1987) Int J Biol Markers. 2:49-53.
DeNardo et al. (1988) Antibody Immunoconj Radiophar. 1:17-33.
Ey et al. (1978) Biochemistry. 15:429-436.
Finer et al. (1994) Blood. 83:43-50.
Frey et al. (1998) Blood. 91:2781-2792.
Greenwood et al. (1993) Eur J Immunol. 23: 1098-1104.
Hirsch and Baruch (2003) Endocrine. 21:201-208.
Hirsch (1964) Science. 146:412-413.
Huston et al. (1988) Proc Natl Acad. Sci. USA. 85:5879-5883.
Jagger et al. (1999) Endocrinology. 140:492-499.
Jagger et al. (2000) Biochem Biophys Res Commun. 274: 124-129.
Jones et al. (1986) Nature. 321, 522-525.
Kimmel (1987) Methods Enzymol. 152:507-511.
Lin et al. (1991) Science. 254:1022-1024.
Mason et al. (2006) Blood Rev. 20:71-82.
Miller et al. (1986) Mol Cell Biol. 6:2895-2902.
Miller et al. (1989) Biotechniques. 7:980-82, 984-86, 989-990.
Morrison et al. (1984) Proc Natl Acad Sci USA, 81:6851-6855.
Pear et al. (1993) Proc Natl Acad Sci USA. 90:8392-8396.
Pastan et al. (1986) Cell. 47:641.
Ramsay and Kersey (1988) J Clin Immunol. 8:81-88.
Ross and Glomset (1973) Science. 180:1332-1339.
Schmidt et al. (1991) J Biol Chem. 266:18025-33.
Sun et al. (1986) Hybridoma 5 Suppl 1:517-20.
Thorpe et al. (1987) Cancer Res. 47:5924.
Tikellis et al. (2003) Kidney International 63:416-426.
Tolcos et al. (2003) J Comp Neurol 456:29-38.
Urlaub and Chasin (1980) Proc Natl Acad Sci USA. 77:4216-4220.
Vitetta et al. (1987) Science. 238: 1098.
Wahl and Berger (1987) Methods Enzymol. 152:399-407.
Waldmann (1991) Science. 252:1657.
Xu et al. (1994) Exp Hemat. 22:223-30.
Zulli et al. (2003) Aterioscler Thromb Vasc Biol. 23:1358-1363.
Zulli et al. (2005) Histochem Cell Biol. 124:517-522.
Zulli et al. (2006) J Histochem Cytochem. 54:151-159.

The claims defining the invention are as follows:

1. An isolated antibody, or fragment thereof, which specifically binds calcitonin receptor, wherein the antibody binds an epitope within SEQ ID NO: 5.

2. The isolated antibody of claim 1, which is a monoclonal antibody.

3. The isolated antibody of claim 2, wherein the antibody is 1C11 or 9B4.

4. The isolated antibody of claim 1, which is delectably labelled.

5. A stable antibody producing cell line which is capable of producing the isolated antibody of claim 2.

6. The cell line of claim 5, which is 1C11 as deposited with the European Collection of Cell Cultures (ECACC) on 10 Aug. 2007 under Deposit Reference 07081002, or 9B4 as deposited with the European Collection of Cell Cultures (ECACC) on 10 Aug. 2007 under accession number 07081001.

7. An isolated antibody that binds to calcitonin receptor, wherein the antibody binds to an epitope within SEQ ID NO: 5, and wherein the antibody competitively inhibits the binding of the monoclonal antibody of claim 3 to calcitonin receptor.

8. The isolated antibody of claim 1, which is conjugated to a cytotoxic agent or a biological response modifier.

9. The isolated antibody of claim 1, which is a chimeric antibody or humanized antibody.

10. A method for diagnosing or detecting leukemia in a subject, the method comprising contacting a sample obtained from a subject suspected of having leukemia with the antibody or fragment thereof of claim 1 and determining the presence or level of calcitonin receptor, wherein the presence and/or increased level of expression of calcitonin receptor is indicative of leukemia.

* * * * *

SEQUENCE LISTING

<160> NUMBER OF SEQ ID NOS: 8

<210> SEQ ID NO 1
<211> LENGTH: 1425
<212> TYPE: DNA
<213> ORGANISM: Homo sapiens

<400> SEQUENCE: 1

```
atgaggttca catttacaag ccggtgcttg cactgttttc ttcttctaaa tcacccaacc      60
ccaattcttc ctgccttttc aaatcaaacc tatccaacaa tagagcccaa gccatttctt     120
tacgtcgtag gacgaaagaa gatgatggat gcacagtaca aatgctatga ccgaatgcag     180
cagttacccg cataccaagg agaaggtcca tattgcaatc gcacctggga tggatggctg     240
tgctgggatg acacaccggc tggagtattg tcctatcagt tctgcccaga ttattttccg     300
gattttgatc catcagaaaa ggttacaaaa tactgtgatg aaaaaggtgt ttggtttaaa     360
catcctgaaa acaatcgaac ctggtccaac tatactatgt gcaatgcttt cactcctgag     420
aaactgaaga atgcatatgt tctgtactat ttggctattg tgggtcattc tttgtcaatt     480
ttcaccctag tgatttccct ggggattttc gtgttttca ggagccttgg ctgccaaagg      540
gtaaccctgc acaagaacat gtttcttact tacattctga attctatgat tatcatcatc     600
cacctggttg aagtagtacc caatggagag ctcgtgcgaa gggacccggt gagctgcaag     660
attttgcatt ttttccacca gtacatgatg gcctgcaact atttctggat gctctgtgaa     720
gggatctatc ttcatacact cattgtcgtg ctgtgtttta ctgagaagca acgcttgcgg     780
tggtattatc tcttgggctg ggggttcccg ctggtgccaa ccactatcca tgctattacc     840
agggccgtgt acttcaatga caactgctgg ctgagtgtgg aaacccattt gctttacata     900
atccatggac ctgtcatggc ggcacttgtg gtcaatttct ctttttgct caacattgtc     960
cgggtgcttg tgaccaaaat gagggaaacc catgaggcgg aatcccacat gtacctgaag    1020
gctgtgaagg ccaccatgat ccttgtgccc ctgctgggaa tccagtttgt cgtcttttcc    1080
tggagacctt ccaacaagat gcttgggaag atatatgatt acgtgatgca ctctctgatt    1140
catttccagg gcttctttgt tgcgaccatc tactgcttct gcaacaatga ggtccaaacc    1200
accgtgaagc gccaatgggc ccaattcaaa attcagtgga accagcgttg ggggaggcgc    1260
ccctccaacc gctctgctcg cgctgcagcc gctgctgcgg aggctggcga catcccaatt    1320
tacatctgcc atcaggagct gaggaatgaa ccagccaaca accaaggcga ggagagtgct    1380
gagatcatcc ctttgaatat catagagcaa gagtcatctg cttga                   1425
```

<210> SEQ ID NO 2
<211> LENGTH: 474
<212> TYPE: PRT
<213> ORGANISM: Homo sapiens

<400> SEQUENCE: 2

Met Arg Phe Thr Phe Thr Ser Arg Cys Leu Ala Leu Phe Leu Leu Leu
1               5                   10                  15

Asn His Pro Thr Pro Ile Leu Pro Ala Phe Ser Asn Gln Thr Tyr Pro
            20                  25                  30

Thr Ile Glu Pro Lys Pro Phe Leu Tyr Val Val Gly Arg Lys Lys Met
        35                  40                  45

Met Asp Ala Gln Tyr Lys Cys Tyr Asp Arg Met Gln Gln Leu Pro Ala
    50                  55                  60

```
Tyr Gln Gly Glu Gly Pro Tyr Cys Asn Arg Thr Trp Asp Gly Trp Leu
 65                  70                  75                  80

Cys Trp Asp Asp Thr Pro Ala Gly Val Leu Ser Tyr Gln Phe Cys Pro
                 85                  90                  95

Asp Tyr Phe Pro Asp Phe Asp Pro Ser Glu Lys Val Thr Lys Tyr Cys
            100                 105                 110

Asp Glu Lys Gly Val Trp Phe Lys His Pro Glu Asn Asn Arg Thr Trp
        115                 120                 125

Ser Asn Tyr Thr Met Cys Asn Ala Phe Thr Pro Glu Lys Leu Lys Asn
    130                 135                 140

Ala Tyr Val Leu Tyr Tyr Leu Ala Ile Val Gly His Ser Leu Ser Ile
145                 150                 155                 160

Phe Thr Leu Val Ile Ser Leu Gly Ile Phe Val Phe Phe Arg Ser Leu
                165                 170                 175

Gly Cys Gln Arg Val Thr Leu His Lys Asn Met Phe Leu Thr Tyr Ile
            180                 185                 190

Leu Asn Ser Met Ile Ile Ile His Leu Val Glu Val Val Pro Asn
    195                 200                 205

Gly Glu Leu Val Arg Arg Asp Pro Val Ser Cys Lys Ile Leu His Phe
210                 215                 220

Phe His Gln Tyr Met Met Ala Cys Asn Tyr Phe Trp Met Leu Cys Glu
225                 230                 235                 240

Gly Ile Tyr Leu His Thr Leu Ile Val Val Ala Val Phe Thr Glu Lys
            245                 250                 255

Gln Arg Leu Arg Trp Tyr Leu Leu Gly Trp Gly Phe Pro Leu Val
    260                 265                 270

Pro Thr Thr Ile His Ala Ile Thr Arg Ala Val Tyr Phe Asn Asp Asn
            275                 280                 285

Cys Trp Leu Ser Val Glu Thr His Leu Leu Tyr Ile Ile His Gly Pro
    290                 295                 300

Val Met Ala Ala Leu Val Val Asn Phe Phe Phe Leu Leu Asn Ile Val
305                 310                 315                 320

Arg Val Leu Val Thr Lys Met Arg Glu Thr His Glu Ala Glu Ser His
                325                 330                 335

Met Tyr Leu Lys Ala Val Lys Ala Thr Met Ile Leu Val Pro Leu Leu
            340                 345                 350

Gly Ile Gln Phe Val Val Phe Pro Trp Arg Pro Ser Asn Lys Met Leu
        355                 360                 365

Gly Lys Ile Tyr Asp Tyr Val Met His Ser Leu Ile His Phe Gln Gly
        370                 375                 380

Phe Phe Val Ala Thr Ile Tyr Cys Phe Cys Asn Asn Glu Val Gln Thr
385                 390                 395                 400

Thr Val Lys Arg Gln Trp Ala Gln Phe Lys Ile Gln Trp Asn Gln Arg
            405                 410                 415

Trp Gly Arg Arg Pro Ser Asn Arg Ser Ala Arg Ala Ala Ala Ala Ala
        420                 425                 430

Ala Glu Ala Gly Asp Ile Pro Ile Tyr Ile Cys His Gln Glu Leu Arg
        435                 440                 445

Asn Glu Pro Ala Asn Asn Gln Gly Glu Glu Ser Ala Glu Ile Ile Pro
    450                 455                 460

Leu Asn Ile Ile Glu Gln Glu Ser Ser Ala
465                 470
```

<210> SEQ ID NO 3

```
<211> LENGTH: 18
<212> TYPE: PRT
<213> ORGANISM: Artificial
<220> FEATURE:
<223> OTHER INFORMATION: epitope

<400> SEQUENCE: 3

Asp Ile Pro Ile Tyr Ile Cys His Gln Glu Leu Arg Asn Glu Pro Ala
1               5                   10                  15

Asn Asn

<210> SEQ ID NO 4
<211> LENGTH: 18
<212> TYPE: PRT
<213> ORGANISM: Artificial
<220> FEATURE:
<223> OTHER INFORMATION: epitope

<400> SEQUENCE: 4

Gly Ile Pro Val Tyr Ile Tyr His Gln Glu Pro Arg Asn Asp Pro Ala
1               5                   10                  15

His Ser

<210> SEQ ID NO 5
<211> LENGTH: 17
<212> TYPE: PRT
<213> ORGANISM: Artificial
<220> FEATURE:
<223> OTHER INFORMATION: epitope

<400> SEQUENCE: 5

Pro Ser Glu Lys Val Thr Lys Tyr Cys Asp Glu Lys Gly Val Trp Phe
1               5                   10                  15

Lys

<210> SEQ ID NO 6
<211> LENGTH: 17
<212> TYPE: PRT
<213> ORGANISM: Artificial
<220> FEATURE:
<223> OTHER INFORMATION: epitope

<400> SEQUENCE: 6

Pro Thr Glu Lys Val Thr Lys Tyr Cys Asp Glu Thr Gly Val Trp Phe
1               5                   10                  15

Lys

<210> SEQ ID NO 7
<211> LENGTH: 12
<212> TYPE: PRT
<213> ORGANISM: Artificial
<220> FEATURE:
<223> OTHER INFORMATION: epitope

<400> SEQUENCE: 7

Phe Ser Asn Gln Thr Tyr Pro Thr Ile Glu Pro Lys
1               5                   10

<210> SEQ ID NO 8
<211> LENGTH: 20
<212> TYPE: PRT
<213> ORGANISM: Artificial
<220> FEATURE:
<223> OTHER INFORMATION: epitope

<400> SEQUENCE: 8
```

```
Lys Gly Leu Pro Ile Tyr Ile Cys His Gln Glu Pro Arg Asn Pro Pro
1               5                   10                  15

Val Ser Asn Asn
            20
```